(12) United States Patent
Force Aldred et al.

(10) Patent No.: US 11,873,336 B2
(45) Date of Patent: Jan. 16, 2024

(54) HEAVY CHAIN ANTIBODIES BINDING TO CD22

(71) Applicant: TeneoBio, Inc., Thousand Oaks, CA (US)

(72) Inventors: Shelley Force Aldred, Thousand Oaks, CA (US); Wim van Schooten, Thousand Oaks, CA (US); Heather Anne N. Ogana, Thousand Oaks, CA (US); Laura Marie Davison, Thousand Oaks, CA (US); Katherine Harris, Thousand Oaks, CA (US); Udaya Rangaswamy, Thousand Oaks, CA (US); Nathan D. Trinklein, Thousand Oaks, CA (US)

(73) Assignee: TENEOBIO, INC., Thousand Oaks, CA (US)

( * ) Notice: Subject to any disclaimer, the term of this patent is extended or adjusted under 35 U.S.C. 154(b) by 0 days.

(21) Appl. No.: 16/956,502

(22) PCT Filed: Dec. 21, 2018

(86) PCT No.: PCT/US2018/067299
§ 371 (c)(1),
(2) Date: Jun. 19, 2020

(87) PCT Pub. No.: WO2019/126756
PCT Pub. Date: Jun. 27, 2019

(65) Prior Publication Data
US 2021/0095022 A1     Apr. 1, 2021

Related U.S. Application Data

(60) Provisional application No. 62/609,759, filed on Dec. 22, 2017.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *C07K 16/2809* (2013.01); *A61K 2039/505* (2013.01); *C07K 2317/31* (2013.01); *C07K 2317/51* (2013.01)

(58) Field of Classification Search
CPC .............................................. C07K 2317/569
See application file for complete search history.

(56) References Cited

U.S. PATENT DOCUMENTS

| | | | |
|---|---|---|---|
| 4,816,567 A | 3/1989 | Cabilly et al. |
| 5,500,362 A | 3/1996 | Robinson et al. |
| 5,821,337 A | 10/1998 | Carter et al. |
| 7,541,513 B2 | 6/2009 | Bruggeman et al. |
| 8,367,888 B2 | 2/2013 | Bruggeman et al. |
| 8,883,150 B2 | 11/2014 | Craig et al. |
| 9,034,324 B2 | 5/2015 | Kalled et al. |
| 9,365,655 B2 | 6/2016 | Craig et al. |
| 2004/0229310 A1 | 11/2004 | Simmons |
| 2005/0048572 A1 | 3/2005 | Reilly et al. |
| 2007/0071675 A1 | 3/2007 | Wu et al. |
| 2010/0122358 A1 | 5/2010 | Brüggemann et al. |
| 2013/0273055 A1 | 10/2013 | Borges et al. |
| 2014/0056897 A1 | 2/2014 | Buelow et al. |
| 2014/0088295 A1 | 3/2014 | Smith et al. |
| 2015/0266966 A1 | 9/2015 | Smith et al. |
| 2015/0368351 A1 | 12/2015 | Vu et al. |
| 2016/0046724 A1 | 2/2016 | Brogdon et al. |
| 2016/0166689 A1 | 6/2016 | Adler et al. |
| 2016/0194399 A1 | 7/2016 | Irving et al. |
| 2016/0355591 A1 | 12/2016 | Goldenberg et al. |
| 2017/0174770 A1 | 6/2017 | Bruggemann et al. |
| 2017/0275363 A1 | 9/2017 | Chang et al. |

FOREIGN PATENT DOCUMENTS

| | | |
|---|---|---|
| CA | 2828347 | 9/2012 |
| CN | 103619876 | 3/2014 |
| CN | 104710528 A | 6/2015 |
| CN | 106029098 A | 10/2016 |
| JP | 2012-504403 | 2/2012 |
| JP | 2013-528569 | 7/2013 |
| JP | 2014515598 | 7/2014 |
| JP | 2015-521032 | 7/2015 |
| RU | 2561457 | 8/2015 |
| RU | 2014147452 | 6/2016 |
| WO | 1996/032478 A1 | 10/1996 |
| WO | 1997/034631 A1 | 9/1997 |
| WO | 2001/077342 | 10/2001 |
| WO | 2006/008548 A2 | 1/2006 |
| WO | 2010/032061 | 3/2010 |
| WO | 2011/097603 | 8/2011 |
| WO | 2012/122512 | 9/2012 |
| WO | 2012/122528 | 9/2012 |
| WO | 2013/072406 | 5/2013 |
| WO | 2013/072415 | 5/2013 |
| WO | 2014/022540 | 2/2014 |
| WO | 2014/047231 | 3/2014 |
| WO | 2014/093908 | 6/2014 |
| WO | 2014/140248 | 9/2014 |
| WO | 2015/095412 | 6/2015 |
| WO | 2015/121383 | 8/2015 |
| WO | 2015/130416 | 9/2015 |

(Continued)

OTHER PUBLICATIONS

Tam et al, Antibodies, 2017, vol. 6, 34 pages (Year: 2017).*

(Continued)

*Primary Examiner* — Karen A. Canella
(74) *Attorney, Agent, or Firm* — Haynes and Boone LLP

(57) ABSTRACT

Anti-CD22 heavy chain antibodies (e.g., UniAbs™) are disclosed, along with methods of making such antibodies, compositions, including pharmaceutical compositions, comprising such antibodies, and their use to treat B cell disorders that are characterized by the expression of CD22.

14 Claims, 18 Drawing Sheets
Specification includes a Sequence Listing.

(56) References Cited

FOREIGN PATENT DOCUMENTS

| WO | 2016/014974 | 1/2016 |
|---|---|---|
| WO | 2016/079081 | 5/2016 |
| WO | 2016/079177 | 5/2016 |
| WO | 2017/134134 | 8/2017 |
| WO | 2017/223111 | 12/2017 |
| WO | 2018/039180 | 3/2018 |
| WO | 2018/039180 A1 | 3/2018 |
| WO | 2018/052503 | 3/2018 |
| WO | 2018/523503 A1 | 3/2018 |
| WO | 2018/119215 | 6/2018 |
| WO | 2018/237006 | 12/2018 |
| WO | 2018/237037 | 12/2018 |
| WO | 2019/006072 | 1/2019 |
| WO | 2019/055689 | 3/2019 |
| WO | 2019/126756 | 6/2019 |
| WO | 2019/133761 | 7/2019 |
| WO | 2020/018922 | 1/2020 |
| WO | 2020/061478 | 3/2020 |
| WO | 2020/087065 | 4/2020 |
| WO | 2020/206330 | 10/2020 |
| WO | 2020/252366 | 12/2020 |
| WO | 2021/127489 | 6/2021 |
| WO | 2021/222578 | 11/2021 |
| WO | 2021/222616 | 11/2021 |
| WO | 2022/006316 | 1/2022 |
| WO | 2022/109010 | 5/2022 |
| WO | 2022/183074 | 9/2022 |
| WO | 2022/183101 | 9/2022 |
| WO | 2022/212848 | 10/2022 |
| WO | 2022/216864 | 10/2022 |
| WO | 2022/221698 | 10/2022 |
| WO | 2022/271987 | 12/2022 |
| WO | 2023/004197 | 1/2023 |

OTHER PUBLICATIONS

Aalberse and Schuurman (Immunology, 2002, vol. 105, pp. 9-19) (Year: 2002).*
Amiri et al., "A Novel Anti-CD22 scFv-apoptin Fusion Protein Induces Apoptosis in Malignant B-cells," (2017) AMB Express 7(112) Abstract.
Buelow et al., "Development of a Fully Human T Cell Engaging Bispecific Antibody for the Treatment of Multiple Myeloma," (2017) retrieved from the Internet: http://www.teneobio.com/wp-content/uploads/2018/01/Poster_1.pdf.
Leow et al., "Single Domain Antibodies as New Biomarker Detectors," (2017) Diagnostics 7(4).
Rangaswamy et al., "A Novel T-cell Bispecific Antibody Platform for Efficient T-cell Mediated Killing of Tumor Cells with Minimal Cytokine Release," (2018) Journal of Clinical Oncology 36(5) Supplement.
Trinklein et al., "Efficient Tumor Killing and Minimal Cytokine Release with Novel T-cell Agonist Bispecific Antibodies," (2019) MABS 11(4):639-652.
Trinklein et al., "Abstract LB-090: Sequence-based Discovery of Fully Human Anti-CD3 and Anti-PDL1 Single Domain Antibodies Using Novel Transgenic Rats," (2016) Cancer Research, retrieved from the Internet: http://cancerres.aacrjournals.org/content/76/14_Supplement/LB-090.
Donelinger et al., "Understanding the Significance and Implications of Antibody Numbering and Antigen-binding Surface/Residue Definition," (2018) Frontiers in Immunology 9(2018):2278.
Faraji et al., "Development and Characterization of a Camelid Single-domain Antibody Directed to Human CD22 Biomarker," Biotechnol Appl Biochem 65.5 (2018): 718-725 (Abstract only).
Janssens et al., "Generation of Heavy-chain-only Antibodies in Mice," PNAS 103.41 (2006): 15130-15135.
Zarei et al., "High Efficient Expression of a Functional Humanized Single-chain Variable Fragment (ScFv) Antibody Against CD22 in Pichia Pastoris," Appl Microbiol Biotechnol 98.24 (2014): 10023-10039 (Abstract only).

Kim et al., "Mutational approaches to improve the biophysical properties of human single-domain antibodies", (2014) Biochimica Et Biophysica ACTA (BBA)—Proteins & Proteomics, Elseviern Netherlands (2014) 1844(11):1983-2001.
Lefranc et al., "The Immunoglobulin FactsBook," (2001).
Bruggemann et al., "Human Antibody Production in Transgenic Animals," (2014) Archivum Immunologiae et Therapie Experimentalis, Birkahaeser Verlag AG 63(2):101-108.
Ménoret et al., "Transgenic Animals and Genetic Engineering Techniques," (2015) Transgenic Res 24:1079-1085.
Baas et al., "Superhuman Mice" (2014) Science-Business exchange 7(17):1-2.
Ippoliti et al., "Immunomodulation with Rabbit Anti-thymocyte Globulin in Solid Organ Transplantation," (2015) World J Transplant 5(4):261-266.
Lloyd et al., "Modeling the Human Immune Response: Performance of a $10^{11}$ Human Antibody Repertoire Against a Broad Panel of Therapeutically Relevant Antigens," (2009) Protein Engineering, Design & Selection 22(3): 159-168.
Goel et al., "Plasticity within the Antigen-combining Site May Manifest as Molecular Mimicry in Humoral Immune Response," (2004) J Immunol 173(12):7358-7367.
Rabia et al., "Understanding and Overcoming Trade-offs between Antibody Affinity, Specificity, Stability and Solubility," (2018) Biochemical Engineering Journal 137:365-374.
Alderson et al., "CAT-8015: A Second-Generation Pseudomonas Exotoxin A—Based Immunotherapy Targeting CD22-Expressing Hematologic Malignancies," (2009) Clinical Cancer Research 15(3):832-839.
Almagro "Identification of differences in the specificity-determining residues of antibodies that recognize antigens of different size: implications for the rational design of antibody repertoires," (2004) Journal of Molecular Recognition 17(2):132-143.
Armitage, "A clinical evaluation of the International Lymphoma Study Group classification of non-Hodgkin's lymphoma," (1997) Blood 89(11):3909-3918.
Armour et al., "Recombinant human IgG molecules lacking Fcγ receptor I binding and monocyte triggering activities," (1999) Eur J Immunol. 29(8):2613-2624.
Boesch et al., "Highly parallel characterization of IgG Fc binding interactions," (2014) MAbs 6(4):915-927.
Bruggemann et al., "Heavy-Chain-Only Antibody Expression and B-Cell Development in the Mouse," (2006) Crit. Rev. Immunol. 26(5):377-90.
Canfield et al."The Binding Affinity of Human IgG for its High Affinity Fc Receptor Is Determined by Multiple Amino Acids in the CH2 Domain and Is Modulated by the Hinge Region," (1991) J Exp Med 173(6):1483-1491.
Chen et al., "Fusion protein linkers: Property, design and functionality," (2013) Advanced Drug Delivery Reviews 65(10): 1357-1369.
Chothia et al., "Conformations of immunoglobulin hypervariable regions," (1989) Nature 342:877-883.
Chothia et al., "Canonical structures for the hypervariable regions of immunoglobulins," (1987) Journal of Molecular Biology 196(4):901-917.
Clynes et al., "Fc Receptors are Required in Passie and Active Immunity to Melanoma," (1998) PNAS (USA) 95(2):652-656.
Concepcion et al., "Label-Free Detection of Biomolecular Interactions Using BioLayer Interferometry for Kinetic Characterization," (2009) Combinatorial Chemistry & High Throughput Screening 12(8):791-800.
Cui et al., "Targeted Integration in Rat and Mouse Embryos with Zinc-finger Nucleases," (2011) Nature Biotechnology 29(1):64-67.
Dai et al., "Chimeric Antigen Receptors Modified T-cells for Cancer Therapy," (2016) J Natl Cancer Inst 108(7):djv439.
Desmyter et al., "Antigen Specificity and High Affinity Binding Provided by One Single Loop of a Camel Single-domain Antibody," (2001) Journal of Biological Chemistry 276(28):26285-26290.
Dooley et al., "Selection and Characterization of Naturally Occurring Single-domain (IgNAR) Antibody Fragments from Immunized Sharks by Phage Display," (2003) Molecular Immunology 40:25-33.

(56) References Cited

OTHER PUBLICATIONS

Duncan et al., "Localization of the binding site for the human high-affinity Fc receptor on IgG ," (1988) Nature 332:563-564.
Frenken et al., "Isolation of Antigen Specific Llama $V_{HH}$ Antibody Fragments and Their High Level Secretion by *Saccharomyces cerevisiae*," (2000) J. Biotechnol. 78:11-21.
Fry et al., "CD22-targeted CAR T Cells Induce Remission in B-ALL that is Naïve or Resistant to CD19-targeted CAR Immunotherapy," (2017) Nature Medicine.
Gazzano-Santoro et al., "A non-radioactive complement-dependent cytotoxicity assay for anti-CD20 monoclonal antibody," (1996) Journal of Immunological Methods 202(2):163-171.
Geurts et al., "Knockout Rats via Embryo Microinjection of Zinc-finger Nucleases," (2009) Science 325(5939):433.
Ghahroudi et al., "Selection and Identification of Single Domain Antibody Fragments from Camel Heavy-chain Antibodies," (1997) FEBS Letters 414:521-526.
Hamers-Casterman et al., "Naturally Occurring Antibodies Devoid of Light Chains," (1993) Letters to Nature 363:446-448.
Hanes et al., "New advances in microsphere-based single-dose vaccines," (1997) Advanced Drug Delivery Reviews 28(1):97-119.
Hassanzadeh-Ghassabeh et al., "Nanobodies and their potential applications," (2013) 8(6):1013-1023.
Honegger, "Yet Another numbering scheme for immunoglobulin variable domains: an automatic modeling and analysis tool," (2001) Journal of Molecular Biology 309(3):657-670.
Iri-Sofla et al., "Nanobody-based Chimeric Receptor Gene Integration in Jurkat Cells Mediated by PhiC31 Integrase," (2011) Experimental Cell Research 317:2630-2641.
Jabbour et al., "Monoclonal Antibodies in Acute Lymphoblastic Leukemia," (2015) Blood 125(26):2010-2016.
Jackson et al., "Driving CAR T-cells forward," (2016) Nature Reviews Clinical Oncology 13:370-383.
Jamnani et al., "T Cells Expressing VHH-directed Oligoclonal Chimeric HER2 Antigen Receptors: Towards Tumor-directed Oligoclonal T Cell Therapy," (2014) Biochimica et Biophysica Acta 1840:378-386.
Jaton et al., "Recovery of Antibody Activity Upon Reoxidation of Completely Reduced Polyalanyl Heavy Chain and its Fd Fragment Derived from Anti-2,4-dinitrophenyl Antibody," (1968) Biochemistry 7(12):4185-4195.
Jones, "Analysis of Polypeptides and Proteins," (1993) Advanced Drug Delivery Reviews 10(1):29-90.
Kohler et al., "Continuous cultures of fused cells secreting antibody of predefined specificity," (1975) Nature 256:495-497.
Langer, "New Methods of Drug Delivery," (1990) Science 249(4976):1527-1533.
Lund et al., "Expression and characterization of truncated forms of humanized L243 IgG1," (2000) European Journal of Biochemistry 267(24):7246-7256.
Menoret et al., "Characterization of Immunoglobulin Heavy Chain Knockout Rats," (2010) European Journal Immunology 40:2932-2941.
Miller et al., "Design, Construction, and In Vitro Analyses of Multivalent Antibodies," (2003) Jour. of Immunology 170(9):4854-4861.
Muyldermans, "Single domain camel antibodies: current status," 2001; Journal of Biotechnology 74(4):277-302.
Nguyen et al., "Heavy-chain only antibodies derived from dromedary are secreted and displayed by mouse B cells," (2003) Immunology; 109(1):93-101.
Nuttall et al., "Isolation and Characterization of an IgNAR Variable Domain Specific for the Human Mitochondrial Translocase Receptor Tom70," (2003) Eur. J. Biochem. 270:3543-3554.
Nuttall et al., "Selection and Affinity Maturation of IgNAR Variable Domains Targeting Plasmodium falciparum AMA1," (2004) Proteins; Structure, Function and Bioinformatics 55:187-197.
Ofran et al. "Automated identification of complementarity determining regions (CDRs) reveals peculiar characteristics of CDRs and B-cell epitopes," (2008) Journal of Immunology 181(9):6230-6235.
Padlan et al., "Identification of specificity-determining residues in antibodies," (1995) FASEB Journal 9(1):133-139.
Ravetch et al., "Fc Receptors," (1991) Annual Review of Immunology 9:457-492.
Reichert et al., "Development Trends for Monoclonal Antibody Cancer Therapeutics," (2007) Nat Rev Drug Discov 6(5):349-356.
Roux et al., "Comparisons of the Ability of Human IgG3 Hinge Mutants, IgM, IgE, and IgA2, to Form Small Immune Complexes: A Role for Flexibility and Geometry," (1998) Journal of Immunology 161(8):4083-4090.
Shields et al., "High Resolution Mapping of the Binding Site on Human IgG1 for FcγRI, FcγRII, FcγRIII, and FcRn and Design of IgG1 Variants with Improved Binding to the FcγR," (2001) J Biol Chem. 276(9):6591-6604.
Sitia et al., "Developmental Regulation of IgM Secretion: The Role of the Carbosy-terminal Cysteine," (1990) Cell, 60:781-790.
Tao et al., "Structural features of human immunoglobulin G that determine isotype-specific differences in complement activation," (1993) Journal of Experimental Medicine 178(2):661-667.
Van der Linden et al., "Comparison of Physical Chemical Properties of Llama $V_{HH}$ Antibody Fragments and Mouse Monoclonal Antibodies," (1999) Biochimica et Biophysica Acta 1431:37-46.
Vincke et al., "General strategy to humanize a camelid single-domain antibody and identification of a universal humanized nanobody scaffold," (2009) J Biol Chem 284(5):32373-3284.
Walker et al., "CD22: An Inhibitory Enigma," (2007) Immunology 123:314-325.
Zhao et al., "A germline knowledge based computational approach for determining antibody complementarity determining regions," (2010) Molecular Immunology 47(4):694-700.
Zou et al., "Heavy Chain-Only Antibodies are Spontaneously Produced in Light Chain-Deficient," (2007) J Exp Med 204(13): 3271-3283.

* cited by examiner

FIG. 1

| SEQ aa CDR1 | SEQ aa CDR2 | SEQ aaCDR3 |
|---|---|---|
| GDSISSGDYY (SEQ ID NO: 1) | IYYSGVT (SEQ ID NO: 11) | TREDSSNWRS (SEQ ID NO: 18) |
| GDSISSGGYY (SEQ ID NO: 2) | IYYSGAT (SEQ ID NO: 12) | TRDDSSNWRS (SEQ ID NO: 19) |
| GGSISSGDYY (SEQ ID NO: 3) | IYYSGST (SEQ ID NO: 13) | TREDSSSWRS (SEQ ID NO: 20) |
| GGSISSSSYY (SEQ ID NO: 4) | IYYTGST (SEQ ID NO: 14) | AREDSSSWRS (SEQ ID NO: 21) |
| GGSFSGYY (SEQ ID NO: 5) | VYYTGAT (SEQ ID NO: 15) | KRDDSSNWRS (SEQ ID NO: 22) |
| GDSISSSSYY (SEQ ID NO: 6) | IHYSGST (SEQ ID NO: 16) | ARDDSSNWRS (SEQ ID NO: 23) |
| GGSITSSSYY (SEQ ID NO: 7) | IYYSGSA (SEQ ID NO: 17) | |
| GGSISSSHY (SEQ ID NO: 8) | | |
| GGSIISSSYY (SEQ ID NO: 9) | | |
| GGSINDNSHY (SEQ ID NO: 10) | | |

FIG. 2

| Clone ID # | SEQ_aa_FR1_FR4 | SEQ ID NO: |
|---|---|---|
| 335207 | QLQLQESGPGLVKPSETLSLTCTVSGDSISSGDYYWGWIRQPPGKGLEWIGHIYYSGVTYYNPSLKSR VTISVDTSRNQFSLKLSSVTAADTAVYYCTREDSSNWRSRGQGTLVTVSS | 24 |
| 335161 | QLQLQESGPGLVKPSETLSLTCTVSGDSISSGDYYWGWIRQPPGKGLEWIGHIYYSGATYYNPSLENR VTISVDTSKNQFSLKLSSVTAADTAVYYCTRDDSSNWRSRGQGTLVTVSS | 25 |
| 335254 | QLQLQESGPGLVKPSETLSLTCTVSGDSISSGDYYWGWIRQPPGKGLEWIGHIYYSGVTYYNPSLKNR VTISVDTSKNQFSLKLSSVTAADTAVYYCTREDSSSWRSRGQGTLVTVSS | 26 |
| 335260 | QLQLQESGPGLVKPSETLSLTCTVSGDSISSGDYYWGWIRQPPGKGLEWIGHIYYSGVTYYNPSLKNR VTISVDTSRNQFSLNLSSVTAADTAVYYCTREDSSSWRSRGQGTLVTVSS | 27 |
| 335151 | QLQLQESGPGLVKPSETLSLTCTVSGDSISSGDYYWGWIRQPPGKGLEWIGHIYYSGATYYNPSLKNR VTISVDTSRNQFSLNLSSVTAADTAVYYCTRDDSSNWRSRGQGTLVTVSS | 28 |
| 335170 | QLQLQESGPGLVKPSETLSLTCTVSGDSISSGDYYWGWIRQPPGKGLEWIGHIYYSGATYYNPSLKNR VTISVDTSRNQFSLKLSSVTAADTAVYYCTRDDSSNWRSRGQGTLVTVSS | 29 |
| 335176 | QLQLQESGPGLVKPSETLSLTCTVSGDSISSGDYYWGWIRQPPGKGLEWIGHIYYSGATYYNPSLKNR VTISVDTSKNQFSLKLSSVTAADTAVYYCTREDSSSWRSRGQGTLVTVSS | 30 |
| 335181 | QLQLQESGPGLVKPSETLSLTCTVSGDSISSGGYYWGWIRQPPGKGLEWIGHIYYSGATYYNPSLKNR VTISVDTSKNQFSLKLSSVTAADTAVYYCTREDSSSWRSRGQGTLVTVSS | 31 |
| 335244 | QLQLQESGPGLVKPSETLSLTCTVSGDSISSGDYYWGWIRQPPGKGLEWIGHIYYSGATYYNPSLKNR VTISVDTSRNQFSLNLSSVTAADTAVYYCTREDSSSWRSRGQGTLVTVSS | 32 |
| 335154 | QLQLQESGPGLVKPSETLSLTCTVSGDSISSGDYYWGWIRQPPGKGLEWIGHIYYSGATYYNPSLKNR VTISVDTSKNQFSLKLSSVTAADTAVYYCTREDSSSWRSRGQGTLVTVSS | 33 |
| 335201 | QLQLQESGPGLVKPSETLSLTCTVSGDSISSGDYYWGWIRQPPGKGLEWIGHIYYSGVTYYNPSLKNR VTISVDTSRNQFSLKLSSVTAADTAVYYCTREDSSSWRSRGQGTLVTVSS | 34 |
| 335261 | QLQLQESGPGLVKPSETLSLTCTVSGDSISSGDYYWGWIRQPPGKGLEWIGHIYYSGATYYNPSLENR VTISVDTSKNQFSLKLSSVTAADTAVYYCTREDSSSWRSRGQGTLVTVSS | 35 |
| 335293 | QLQLQESGPGLVKPSETLSLTCTVSGDSISSGDYYWGWIRQPPGKGLEWIGHIYYSGATYYNPSLKNR VTISVDTSKNQFSLKLSSVTAADTAVYYCTREDSSSWRSRGQGTLVTVSS | 36 |
| 335203 | QLQLQESGPGLVKPSETLSLTCTVSGDSISSGDYYWGWIRQPPGKGLEWIGHIYYSGVTYYNPSLKNR VTISVDTSKNQFSLKLSSVTAADTAVYYCTREDSSSWRSRGQGTLVTVSS | 37 |

FIG. 2 (cont)

| Clone ID # | SEQ_aa_FR1_FR4 | SEQ ID NO: |
|---|---|---|
| 335185 | QLQLQESGPGLVKPSETLSLTCTVSGDSISSGDYYWGWIRQPPGKGLEWIGHIYYSGATYYNPSLKNR VTISVDTSRNQFSLNLSSVTAADTAVYYCTREDSSNWRSRGQGTLVTVSS | 38 |
| 335206 | QLQLQESGPGLVKPSETLSLTCTVSGDSISSGDYYWGWIRQPPGKGLEWIGHIYYSGATYYNPSLKNR VTISVDTSKNQFSLKLSSVTAADTAVYYCTREDSSNWRSRGQGTLVTVSS | 39 |
| 335245 | QLQLQESGPGLVKPSETLSLTCTVSGDSISSGDYYWGWIRQPPGKGLEWIGHIYYSGATYYNPSLKNR VTISVDTSKNQFSLKLSSVTAADTAVYYCTREDSSNWRSRGQGTLVTVSS | 40 |
| 335218 | QLQLQESGPGLVKPSETLSLTCTVSGDSISSGDYYWGWIRQPPGKGLEWIGHIYYSGATYYNPSLKNR VTISVDTSRNQFSLKLSSVTAADTAVYYCTREDSSNWRSRGQGTLVTVSS | 41 |
| 335160 | QLQLQESGPGLVKPSETLSLTCTVSGDSISSGDYYWGWIRQPPGKGLEWIGSIYYSGATYYNPSLKNR VTISVDTSRNQFSLKLSSVTAADTAVYYCTREDSSNWRSRGQGTLVTVSS | 42 |
| 335158 | QLQLQESGPGLVKPSETLSLTCTVSGDSISSGDYYWGWIRQPPGKGLEWIGHIYYSGATYYNPSLKNR VTISVDTSRNQFSLKLSSVTAADTAVYYCTRDDSSNWRSRGQGTLVTVSS | 43 |
| 324508 | QLQLQESGPGLVKPSETLSLTCTVSGGSISSGDYYWGWIRQPPGKGLEWIGHIYYSGATYYNPSLENR VTISVDTSKNQFSLKLSSVTAADTAVYYCTRDDSSNWRSRGQGTLVTVSS | 44 |
| 335307 | QLQLQESGPGLVKPSETLSLTCTVSGDSISSGDYYWGWIRQPPGKGLEWIGSIYYSGATYYNPSLKSRV TISVDTSKNQFSLKLSSVTAADTAVYYCTREDSSSWRSRGQGTLVTVSS | 45 |
| 335301 | QLQLQESGPGLVKPSETLSLTCTVSGDSISSGDYYWGWIRQPPGKGLEWIGNIYYSGATYYNPSLKNR VTISVDTSKNQFSLKLSSVTAADTAVYYCTREDSSNWRSRGQGTLVTVSS | 46 |
| 335323 | QLQLQESGPGLVKPSETLSLTCTVSGDSISSGGYYWGWIRQPPGKGLEWIGSIYYSGTYYNPSLKNR VTISVDTSKNQFSLKLSSVTAADTAVYYCTREDSSSWRSRGQGTLVTVSS | 47 |
| 335271 | QLQLQESGPGLVKPSETLSLTCTVSGDSISSGDYYWGWIRHPPGKGLEWIGHIYYSGATYYNPSLKNR VTISVDTSKNQFSLKLSSVTAADTAVYYCTREDSSNWRSRGQGTLVTVSS | 48 |
| 335234 | QLQLQESGPGLVKPSETLSLTCTVSGDSISSGDYYWGWIRQPPGKGLEWIGNIYYSGATYYNPSLKNR VTISVDTSKNQFSLKLSSVTAADTAVYYCTREDSSNWRSRGQGTLVTVSS | 49 |
| 335182 | QLQLQESGPGLVKPSETLSLTCTVSGDSISSGDYYWGWIRQPPGKGLEWIGNIYYSGATYYNPSLKNR VTISVDTSKNQFSLKLSSVTAADTAVYYCTREDSSNWRSRGQGTLVTVSS | 50 |
| 335186 | QLQLQESGPGLVKPSETLSLTCTVSGGSISSSYYWGWIRQPPGKGLEWIGSIYYSGSTYYNPSLKSRV TISVDTSKNQFSLKLSSVTAADTAVYYCTRDDSSNWRSRGQGTLVTVSS | 51 |
| 335233 | QLQLQESGPGLVKPSETLSLTCTVSGDSISSGDYYWGWIRQPPGKGLEWIGSIYYSGSTYYNPSLKSRV TISVDTSKNQFSLKLSSVTAADTAVYYCTREDSSNWRSRGQGTLVTVSS | 52 |

FIG. 2 (cont)

| Clone ID # | SEQ_aa_FR1_FR4 | SEQ ID NO: |
|---|---|---|
| 335224 | QLQLQESGPGLVKPSETLSLTCTVSGDSISSGDYYWGWIRQPPGKGLEWIGSIYYTGSTYYNPSLKSRVTISVDTSKNQFSLKLSSVTAADTAVYYCTREDSSNWRSRGQGTLVTVSS | 53 |
| 335210 | QLQLQESGPGLVKPSETLSLTCTVSGGSISSGDYYWGWIRQPPGKGLEWIGHIYYSGATYYNPSLKNRVTISVDTSRNQFSLKLSSVTAADTAVYYCTREDSSNWRSRGQGTLVTVSS | 54 |
| 335311 | QLQLQESGPGLVKPSETLSLTCAVYGGSFSGYYWGWIRQPPGKGLEWIGHIYYSGVTYYNPSLKNRVTISVDTSRNQFSLNLSSVTAADTAVYYCTREDSSSWRSRGQGTLVTVSS | 55 |
| 335159 | QLQLQESGPGLVKPSETLSLTCTVSGGSISSSYYWGWIRQPPGKGLEWIGHIYYSGVTYYNPSLKNRVTISVDTSKNQFSLKLSSVTAADTAAYYCTRDDSSNWRSRGQGTLVTVSS | 56 |
| 335188 | QLQLQESGPGLVKPSETLSLTCTVSGGSISSSYYWGWIRQPPGKGLEWIGSIYYSGSTYYNPSLKSRVTISVDTSKNQFSLKLSSVTAADTAVYYCTREDSSNWRSRGQGTLVTVSS | 57 |
| 335274 | QLQLQESGPGLVKPSETLSLTCTVSGDSISSSYYWGWIRQPPGKGLEWIGSIYYSGSTYYNPSLKNRVTISVDTSRNQFSLNLSSVTAADTAVYYCTREDSSNWRSRGQGTLVTVSS | 58 |
| 335226 | QLQLQESGPGLVKPSETLSLTCTVSGGSISSSYYWGWIRQPPGKGLEWIGSIYYSGSTYYNPSLKNRVTISVDTSKNQFSLKLSSVTAADTAVYYCTREDSSNWRSRGQGTLVTVSS | 59 |
| 335333 | QLQLQESGPGLVKPSETLSLTCTVSGGSISSSYYWGWIRQPPGKGLEWIGSIYYSGSTYYNPSLKSRVTISVDTSKNQFSLKLSSVTAADTAVYYCAREDSSSWRSRGQGTLVTVSS | 60 |
| 335283 | QLQLQESGPGLVKPSETLSLTCTVSGGSISSSYYWGWIRQPPGKGLEWIGSIYYSGSTYYNPSLKNRVTISVDTSKNQFSLKLSSVTAADTAVYYCTREDSSSWRSRGQGTLVTVSS | 61 |
| 335297 | QLQLQESGPGLVKPSETLSLTCTVSGGSISSSYYWGWIRQPPGKGLEWIGHIYYSGATYYNPSLKNRVTISVDTSRNQFSLNLSSVTAADTAVYYCTREDSSSWRSRGQGTLVTVSS | 62 |
| 335273 | QLQLQESGPGLVKPSETLSLTCTVSGGSISSSYYWGWIRQPPGKGLEWIGHIYYSGATYYNPSLKNRVTISVDTSKNQFSLKLSSVTAADTAVYYCTREDSSNWRSRGQGTLVTVSS | 63 |
| 335187 | QLQLQESGPGLVKPSETLSLTCTVSGGSISSSYYWGWIRQPPGKGLEWIGHIYYSGATYYNPSLKNRVTISVDTSKNQFSLKLSSVTAADTAVYYCTREDSSNWRSRGQGTLVTVSS | 64 |
| 335295 | QLQLQESGPGLVKPSETLSLTCTVSGGSISSSYYWGWIRQPPGKGLEWIGSIYYSGATYYNPSLKNRVTISVDTSRNQFSLNLSSVTAADTAVYYCTREDSSSWRSRGQGTLVTVSS | 65 |
| 335220 | QLQLQESGPGLVKPSETLSLTCTVSGGSISSSYYWGWIRQPPGKGLEWIGSIYYSGSTYYNPSLKNRVTISVDTSKNQFSLKLSSVTAADTAVYYCTREDSSNWRSRGQGTLVTVSS | 66 |
| 335173 | QLQLQESGPGLVKPSETLSLTCTVSGGSITSSYYWGWIRQPPGKGLEWIGSIYYSGSTYYNPSLKSRVTISVDTSKNQFSLKLSSVTAADTAVYYCTRDDSSNWRSRGQGTLVTVSS | 67 |

FIG. 2 (cont)

| Clone ID # | SEQ_aa_FR1_FR4 | SEQ ID NO: |
|---|---|---|
| 335219 | QLQLQESGPGLVKPSETLSLTCTVSGGSISSSSYYWGWIRQPPGKGLEWIGSIYYSGVTYYNPSLKNRV TISVDTSKNQFSLKLSSVTAADTAVYYCTREDSSNWRSRGQGTLVTVSS | 68 |
| 335236 | QLQLQESGPGLVKPSETLSLTCTVSGGSISSSSYYWGWIRQPPGKGLEWIGSIYYSGSTYYNPSLKSRV TISVDTSKNQFSLKLSSVTAADTAVYYCTREDSSNWRSRGQGTLVTVSS | 69 |
| 335266 | QLQLQESGPGLVRPSETLSLTCTVSGGSISSSSYYWGWIRQPPGKGLEWIGSIYYSGSTYYNPSLKSRV TISVDTSKNQFSLKLSSVTAADTAVYYCTREDSSWRSRGQGTLVTVSS | 70 |
| 335208 | QLQLQESGPGLVKPSETLSLTCTVSGGSISSSSYYWGWIRQPPGKGLEWIGSIYYSGATYYNPSLKNRV TISVDTSRNQFSLNLSSVTAADTAVYYCTREDSSNWRSRGQGTLVTVSS | 71 |
| 335195 | QLQLQESGPGLVKPSETLSLTCTVSGGSISSSSYYWGWIRQPPGKGLEWIGSIYYSGATYYNPSLKNRV TISVDTSRNQFSLNLSSVTAADTAMYYCTREDSSNWRSRGQGTLVTVSS | 72 |
| 335285 | QLQLQESGPGLVKPSETLSLTCTVSGGSISSSSYYWGWIRQPPGKGLEWIGSIYYSGVTYYNPSLKNRV TISVDTSKNQFSLKLSSVTAADTAVYYCTREDSSWRSRGQGTLVTVSS | 73 |
| 335150 | QLQLQESGPGLVKPSETLSLTCIVSGGSISSSGDYYWGWIRQSPEKGLEWIGHIYYSGVTYYNPSLKNR VTISVDTSKNQFSLKLSSVTAADTAVYYCKRDDSSNWRSRGQGTLVTVSS | 74 |
| 335316 | QLQLQESGPGLVKPSETLSLTCTVSGGSISSSSYYWGWIRQPPGKGLEWIGHIYYSGATYYNPSLKNR VTISVDTSKNQFSLKLSSVTAADTAVYYCTREDSSWRSRGQGTLVTVSS | 75 |
| 335189 | QLQLQESGPGLVKPSETLSLTCTVSGGSISSSSYYWGWIRQPPGKGLEWIGSVYYTGATYYNPSLKNR VTISVDTSKNQFSLKLSSVTAADTAVYYCTRDDSSNWRSRGQGTLVTVSS | 76 |
| 335179 | QLQLQESGPGLVKPSETLSLTCTVSGGSISSSSYYWGWFRHPPGKGLDWIGSIHYSGSTYYNPSLKSRV TISVDTSRNQFSLNLSSVTAADTAVYYCTRDDSSNWRSRGQGTLVTVSS | 77 |
| 335230 | QLQLQESDPGLVKPSETLSLTCTVSGGSISSSSHYWGWIRQPPGKGLEWIGHIYYSGATYYNPSLKNR VTISVDTSRNQFSLNLSSVTAADTAVYYCTRDDSSNWRSRGQGTLVTVSS | 78 |
| 335166 | QLQLQESGPGLVKPSETLSLTCTVSGGSISSSSYYWGWIRQPPGKGLEWIGSIYYSGSTYYNPSLKNRV TISVDTSRNQFSLNLSSVTAADTAVYYCTRDDSSNWRSRGQGTLVTVSS | 79 |
| 335242 | QLQLQESGPGLVKPSETLSLTCTVSGGSISSSSYYWGWIRQPPGKGLEWIGHIYYSGATYYNPSLKNR VTISVDTSRNQFSLNLSSVTAADTAVYYCTRDDSSNWRSRGQGTLVTVSS | 80 |
| 335162 | QLQLQESGPGLVKPSETLSLTCTVSGGSIISSSYYWGWIRQPPGKGLEWIGSIYYSGAVYHPSLKSRV TISIDTSKNQFSLKLSSVTAADTAVYYCARDDSSNWRSRGQGTLVTVSS | 81 |
| 335171 | QLQLQESGPGLVKPSETLSLTCTVSGGSISSSSYYWGWIRQPPGKGLEWIGSIYYSGATYYNPSLKNRV TISVDTSRNQFSLNLSSVTAADTAVYYCTRDDSSNWRSRGQGTLVTVSS | 82 |

FIG. 2 (cont)

| Clone ID # | SEQ_aa_FR1_FR4 | SEQ ID NO: |
|---|---|---|
| 335232 | QLQLQESGPGLVKPSETLSLTCTVSGDSISSGDYYWGWIRQPPGKGLEWIGHIYYSGATYYNPSLKNRVTISVDTSRNQSSLNLSSVTAADTAVYYCTREDSSNWRSRGQGTLVTVSS | 83 |
| 335263 | QLQLQESGPGLVKPSETLSLTCTVSGGSINDNSHYWGWIRQPPGKGLEWIGHIYYSGATYYNPSLKNRVTISVDTSRNQFSLNLSSVTAADTAVYYCTREDSSSWRSRGQGTLVTVSS | 84 |

FIG. 3

| Clone ID # | SEQ_aa_CDR1 | SEQ_aa_CDR2 | SEQ_aaCDR3 |
|---|---|---|---|
| 335207 | GDSISSGDYY (SEQ ID NO: 1) | IYYSGVT (SEQ ID NO: 11) | TREDSSNWRS (SEQ ID NO: 18) |
| 335161 | GDSISSGDYY (SEQ ID NO: 1) | IYYSGAT (SEQ ID NO: 12) | TRDDSSNWRS (SEQ ID NO: 19) |
| 335254 | GDSISSGDYY (SEQ ID NO: 1) | IYYSGVT (SEQ ID NO: 11) | TREDSSSWRS (SEQ ID NO: 20) |
| 335260 | GDSISSGDYY (SEQ ID NO: 1) | IYYSGVT (SEQ ID NO: 11) | TREDSSSWRS (SEQ ID NO: 20) |
| 335151 | GDSISSGDYY (SEQ ID NO: 1) | IYYSGAT (SEQ ID NO: 12) | TRDDSSNWRS (SEQ ID NO: 19) |
| 335170 | GDSISSGDYY (SEQ ID NO: 1) | IYYSGAT (SEQ ID NO: 12) | TRDDSSNWRS (SEQ ID NO: 19) |
| 335176 | GDSISSGGYY (SEQ ID NO: 2) | IYYSGAT (SEQ ID NO: 12) | TRDDSSNWRS (SEQ ID NO: 19) |
| 335181 | GDSISSGGYY (SEQ ID NO: 2) | IYYSGAT (SEQ ID NO: 12) | TRDDSSNWRS (SEQ ID NO: 19) |
| 335244 | GDSISSGDYY (SEQ ID NO: 1) | IYYSGVT (SEQ ID NO: 11) | TREDSSSWRS (SEQ ID NO: 20) |
| 335154 | GDSISSGDYY (SEQ ID NO: 1) | IYYSGAT (SEQ ID NO: 12) | TREDSSNWRS (SEQ ID NO: 18) |
| 335201 | GDSISSGDYY (SEQ ID NO: 1) | IYYSGVT (SEQ ID NO: 11) | TREDSSNWRS (SEQ ID NO: 18) |
| 335261 | GDSISSGDYY (SEQ ID NO: 1) | IYYSGAT (SEQ ID NO: 12) | TREDSSSWRS (SEQ ID NO: 20) |
| 335293 | GDSISSGDYY (SEQ ID NO: 1) | IYYSGAT (SEQ ID NO: 12) | TREDSSSWRS (SEQ ID NO: 20) |
| 335203 | GDSISSGDYY (SEQ ID NO: 1) | IYYSGVT (SEQ ID NO: 11) | TREDSSNWRS (SEQ ID NO: 18) |
| 335185 | GDSISSGDYY (SEQ ID NO: 1) | IYYSGAT (SEQ ID NO: 12) | TREDSSNWRS (SEQ ID NO: 18) |
| 335206 | GDSISSGDYY (SEQ ID NO: 1) | IYYSGAT (SEQ ID NO: 12) | TREDSSNWRS (SEQ ID NO: 18) |
| 335245 | GDSISSGDYY (SEQ ID NO: 1) | IYYSGAT (SEQ ID NO: 12) | TREDSSSWRS (SEQ ID NO: 20) |
| 335218 | GDSISSGDYY (SEQ ID NO: 1) | IYYSGAT (SEQ ID NO: 12) | TREDSSNWRS (SEQ ID NO: 18) |
| 335160 | GDSISSGDYY (SEQ ID NO: 1) | IYYSGAT (SEQ ID NO: 12) | TRDDSSNWRS (SEQ ID NO: 19) |
| 335158 | GGSISSGDYY (SEQ ID NO: 3) | IYYSGAT (SEQ ID NO: 12) | TRDDSSNWRS (SEQ ID NO: 19) |
| 324508 | GGSISSGDYY (SEQ ID NO: 3) | IYYSGAT (SEQ ID NO: 12) | TREDSSSWRS (SEQ ID NO: 20) |
| 335307 | GDSISSGDYY (SEQ ID NO: 1) | IYYSGST (SEQ ID NO: 13) | TREDSSSWRS (SEQ ID NO: 20) |
| 335301 | GDSISSGDYY (SEQ ID NO: 1) | IYYSGST (SEQ ID NO: 13) | TREDSSSWRS (SEQ ID NO: 20) |
| 335323 | GDSISSGGYY (SEQ ID NO: 2) | IYYSGAT (SEQ ID NO: 12) | TREDSSSWRS (SEQ ID NO: 20) |
| 335271 | GDSISSGDYY (SEQ ID NO: 1) | IYYSGAT (SEQ ID NO: 12) | TREDSSSWRS (SEQ ID NO: 20) |
| 335234 | GDSISSGDYY (SEQ ID NO: 1) | IYYSGAT (SEQ ID NO: 12) | TREDSSNWRS (SEQ ID NO: 18) |
| 335182 | GDSISSGDYY (SEQ ID NO: 1) | IYYSGAT (SEQ ID NO: 12) | TRDDSSNWRS (SEQ ID NO: 19) |
| 335186 | GGSISSSSYY (SEQ ID NO: 4) | IYYSGST (SEQ ID NO: 13) | TRDDSSNWRS (SEQ ID NO: 19) |

FIG. 3 (cont.)

| Clone ID # | SEQ_aa_CDR1 | SEQ_aa_CDR2 | SEQ_aaCDR3 |
|---|---|---|---|
| 335233 | GDSISSGDYY (SEQ ID NO: 1) | IYYSGST (SEQ ID NO: 13) | TREDSSNWRS (SEQ ID NO: 18) |
| 335224 | GDSISSGDYY (SEQ ID NO: 1) | IYYTGST (SEQ ID NO: 14) | TREDSSNWRS (SEQ ID NO: 18) |
| 335210 | GGSISSGDYY (SEQ ID NO: 3) | IYYSGAT (SEQ ID NO: 12) | TREDSSNWRS (SEQ ID NO: 18) |
| 335311 | GGSFSGYY (SEQ ID NO: 5) | IYYSGAT (SEQ ID NO: 12) | TREDSSSWRS (SEQ ID NO: 20) |
| 335159 | GGSISSSSYY (SEQ ID NO: 4) | IYYSGVT (SEQ ID NO: 11) | TRDDSSNWRS (SEQ ID NO: 19) |
| 335188 | GGSISSSSYY (SEQ ID NO: 4) | IYYSGVT (SEQ ID NO: 11) | TRDDSSNWRS (SEQ ID NO: 19) |
| 335274 | GDSISSSSYY (SEQ ID NO: 6) | IYYSGST (SEQ ID NO: 13) | TREDSSSWRS (SEQ ID NO: 20) |
| 335226 | GGSISSSSYY (SEQ ID NO: 4) | IYYSGST (SEQ ID NO: 13) | TREDSSNWRS (SEQ ID NO: 18) |
| 335333 | GGSISSSSYY (SEQ ID NO: 4) | IYYSGAT (SEQ ID NO: 12) | AREDSSNWRS (SEQ ID NO: 21) |
| 335283 | GGSISSSSYY (SEQ ID NO: 4) | IYYSGAT (SEQ ID NO: 12) | TREDSSSWRS (SEQ ID NO: 20) |
| 335297 | GGSISSSSYY (SEQ ID NO: 4) | IYYSGST (SEQ ID NO: 13) | TREDSSSWRS (SEQ ID NO: 20) |
| 335273 | GGSISSSSYY (SEQ ID NO: 4) | IYYSGST (SEQ ID NO: 13) | TREDSSSWRS (SEQ ID NO: 20) |
| 335187 | GGSISSSSYY (SEQ ID NO: 4) | IYYSGST (SEQ ID NO: 13) | TRDDSSNWRS (SEQ ID NO: 19) |
| 335295 | GGSISSSSYY (SEQ ID NO: 4) | IYYSGAT (SEQ ID NO: 12) | TREDSSSWRS (SEQ ID NO: 20) |
| 335220 | GGSITSSSYY (SEQ ID NO: 7) | IYYSGST (SEQ ID NO: 13) | TRDDSSNWRS (SEQ ID NO: 19) |
| 335173 | GGSISSSSYY (SEQ ID NO: 4) | IYYSGVT (SEQ ID NO: 11) | TREDSSNWRS (SEQ ID NO: 18) |
| 335219 | GGSISSSSYY (SEQ ID NO: 4) | IYYSGST (SEQ ID NO: 13) | TRDDSSNWRS (SEQ ID NO: 19) |
| 335236 | GGSISSSSYY (SEQ ID NO: 4) | IYYSGST (SEQ ID NO: 13) | TREDSSNWRS (SEQ ID NO: 18) |
| 335266 | GDSISSGDYY (SEQ ID NO: 1) | IYYSGVT (SEQ ID NO: 11) | TREDSSSWRS (SEQ ID NO: 20) |
| 335208 | GGSISSSSYY (SEQ ID NO: 4) | IYYSGST (SEQ ID NO: 13) | TREDSSNWRS (SEQ ID NO: 18) |
| 335195 | GGSISSSSYY (SEQ ID NO: 4) | IYYSGAT (SEQ ID NO: 12) | TREDSSNWRS (SEQ ID NO: 18) |
| 335285 | GGSISSSSYY (SEQ ID NO: 4) | IYYSGVT (SEQ ID NO: 11) | TREDSSSWRS (SEQ ID NO: 20) |
| 335150 | GGSISSSSYY (SEQ ID NO: 4) | IYYSGAT (SEQ ID NO: 12) | KRDDSSNWRS (SEQ ID NO: 22) |
| 335316 | GGSISSSSYY (SEQ ID NO: 4) | VVYTGAT (SEQ ID NO: 15) | TREDSSSWRS (SEQ ID NO: 20) |
| 335189 | GGSISSSSYY (SEQ ID NO: 4) | IHYSGST (SEQ ID NO: 16) | TRDDSSNWRS (SEQ ID NO: 19) |
| 335179 | GGSISSSHY (SEQ ID NO: 8) | IYYSGAT (SEQ ID NO: 12) | TREDSSNWRS (SEQ ID NO: 18) |
| 335230 | GGSISSSSYY (SEQ ID NO: 4) | IYYSGST (SEQ ID NO: 13) | TRDDSSNWRS (SEQ ID NO: 19) |
| 335166 | GGSISSSSYY (SEQ ID NO: 4) | IYYSGAT (SEQ ID NO: 12) | TREDSSNWRS (SEQ ID NO: 18) |
| 335242 | GGSISSSSYY (SEQ ID NO: 4) | IYYSGST (SEQ ID NO: 13) | TRDDSSNWRS (SEQ ID NO: 19) |
| 335162 | GGSIISSSYY (SEQ ID NO: 9) | IYYSGSA (SEQ ID NO: 17) | ARDDSSNWRS (SEQ ID NO: 23) |

FIG. 3 (cont)

| Clone ID # | SEQ_aa_CDR1 | SEQ_aa_CDR2 | SEQ_aaCDR3 |
|---|---|---|---|
| 335171 | GGSISSSSYY (SEQ ID NO: 4) | IYYSGAT (SEQ ID NO: 12) | TRDDSSNWRS (SEQ ID NO: 19) |
| 335232 | GDSISSGDYY (SEQ ID NO: 1) | IYYSGAT (SEQ ID NO: 12) | TREDSSNWRS (SEQ ID NO: 18) |
| 335263 | GGSINDNSHY (SEQ ID NO: 10) | IYYSGAT (SEQ ID NO: 12) | TREDSSSWRS (SEQ ID NO: 20) |

FIG. 4

| Clone ID # | KD (M) | Kdis (1/s) | Daudi binding | CHO_cyCD22 | CHO_cyOFFtgt |
|---|---|---|---|---|---|
| 335161 | 2.66E-09 | 2.40E-04 | 811.0 | 208.0 | 5.2 |
| 335254 | 2.83E-09 | 2.45E-04 | 733.0 | 194.0 | 5.1 |
| 335260 | 3.17E-09 | 2.75E-04 | 725.0 | 185.0 | 5.1 |
| 335207 | 3.24E-09 | 2.94E-04 | 776.0 | 209.0 | 5.3 |
| 335151 | 3.77E-09 | 3.21E-04 | 861.0 | 222.0 | 5.3 |
| 335170 | 6.50E-09 | 3.40E-04 | 791.0 | 181.0 | 5.3 |
| 335176 | 4.62E-09 | 3.79E-04 | 848.0 | 212.0 | 5.3 |
| 335181 | 9.44E-09 | 4.43E-04 | 809.0 | 234.0 | 5.4 |
| 335244 | 5.07E-09 | 4.45E-04 | 752.0 | 198.0 | 5.2 |
| 335154 | 5.41E-09 | 4.46E-04 | 837.0 | 232.0 | 5.3 |
| 335201 | 5.19E-09 | 4.67E-04 | 761.0 | 199.0 | 5.5 |
| 335261 | 5.27E-09 | 5.10E-04 | 748.0 | 181.0 | 5.1 |
| 324510 | 6.42E-09 | 5.54E-04 | 690.0 | 172.0 | 5.2 |
| 335293 | 7.41E-09 | 5.57E-04 | 742.0 | 179.0 | 5.3 |
| 335203 | 6.80E-09 | 6.41E-04 | 729.0 | 194.0 | 5.3 |
| 335185 | 8.43E-09 | 6.47E-04 | 754.0 | 220.0 | 5.5 |
| 324317 | 8.48E-09 | 6.58E-04 | 709.0 | 173.0 | 5.2 |
| 335206 | 7.53E-09 | 6.90E-04 | 735.0 | 189.0 | 5.3 |
| 335245 | 7.44E-09 | 7.02E-04 | 742.0 | 192.0 | 5.4 |
| 335218 | 8.91E-09 | 7.05E-04 | 711.0 | 204.0 | 5.1 |
| 335160 | 8.51E-09 | 7.24E-04 | 750.0 | 218.0 | 5.2 |
| 335158 | 4.23E-08 | 8.01E-04 | 883.0 | 193.0 | 5.4 |
| 324508 | 1.25E-08 | 8.28E-04 | 839.0 | 162.0 | 5.2 |
| 335307 | 1.03E-08 | 1.02E-03 | 737.0 | 176.0 | 5.0 |
| 335301 | 1.26E-08 | 1.29E-03 | 716.0 | 166.0 | 5.0 |
| 335323 | 1.41E-08 | 1.30E-03 | 720.0 | 169.0 | 5.3 |
| 335271 | 2.16E-08 | 1.31E-03 | 711.0 | 147.0 | 5.2 |
| 335234 | 1.24E-08 | 1.37E-03 | 734.0 | 161.0 | 5.2 |
| 335182 | 2.24E-08 | 1.58E-03 | 750.0 | 192.0 | 5.3 |

FIG. 4 (cont)

| Clone ID # | KD (M) | Kdis (1/s) | Daudi binding | CHO_cyCD22 | CHO_cyOFFtgt |
|---|---|---|---|---|---|
| 335186 | 1.76E-08 | 1.72E-03 | 402.0 | 33.5 | 5.5 |
| 335233 | 1.90E-08 | 2.01E-03 | 697.0 | 166.0 | 5.3 |
| 335224 | 2.34E-08 | 2.07E-03 | 689.0 | 173.0 | 5.4 |
| 335210 | 6.25E-08 | 2.28E-03 | 735.0 | 159.0 | 5.2 |
| 335311 | 2.66E-09 | 2.77E-03 | 151.0 | 11.7 | 5.1 |
| 335159 | 1.61E-08 | 3.58E-03 | 532.0 | 61.7 | 5.4 |
| 335188 | 5.30E-08 | 4.12E-03 | 663.0 | 113.0 | 5.3 |
| 335274 | 2.36E-08 | 4.30E-03 | 414.0 | 26.0 | 5.1 |
| 335226 | 2.55E-08 | 4.37E-03 | 221.0 | 12.0 | 5.2 |
| 335333 | 2.24E-08 | 4.37E-03 | 372.0 | 21.2 | 5.0 |
| 335283 | 3.69E-08 | 4.57E-03 | 513.0 | 42.4 | 5.2 |
| 335297 | 2.88E-08 | 4.80E-03 | 107.0 | 12.3 | 5.2 |
| 335273 | 4.22E-08 | 4.87E-03 | 385.0 | 23.1 | 5.2 |
| 335187 | 1.28E-07 | 5.12E-03 | 531.0 | 60.7 | 6.0 |
| 335295 | 3.16E-08 | 5.21E-03 | 491.0 | 43.8 | 5.1 |
| 335220 | 4.82E-08 | 5.31E-03 | 322.0 | 18.4 | 5.4 |
| 335173 | 3.05E-08 | 5.43E-03 | 393.0 | 26.7 | 5.5 |
| 335219 | 9.06E-08 | 5.50E-03 | 590.0 | 76.2 | 5.2 |
| 335236 | 2.73E-08 | 5.62E-03 | 338.0 | 18.4 | 5.3 |
| 335266 | 3.85E-08 | 5.79E-03 | 411.0 | 29.2 | 5.1 |
| 335208 | 5.84E-08 | 5.93E-03 | 452.0 | 34.0 | 5.4 |
| 335195 | 1.50E-07 | 5.99E-03 | 420.0 | 33.0 | 5.4 |
| 335285 | 1.14E-07 | 6.07E-03 | 620.0 | 94.7 | 5.1 |
| 335150 | 1.41E-08 | 6.08E-03 | 86.3 | 8.8 | 5.2 |
| 335316 | 2.35E-08 | 6.62E-03 | 103.0 | 9.6 | 5.1 |
| 335189 | 3.60E-08 | 6.92E-03 | 410.0 | 28.6 | 5.3 |
| 335179 | 1.48E-07 | 8.91E-03 | 88.8 | 10.5 | 5.5 |
| 335230 | 7.52E-08 | 8.92E-03 | 47.1 | 7.8 | 5.3 |
| 335166 | 3.30E-08 | 9.15E-03 | 422.0 | 35.5 | 5.2 |
| 335242 | 7.97E-08 | 9.30E-03 | 136.0 | 11.3 | 5.2 |
| 335162 | 9.96E-08 | 9.41E-03 | 23.3 | 9.1 | 5.2 |

FIG. 4 (cont)

| Clone ID # | KD (M) | Kdis (1/s) | Daudi binding | CHO_cyCD22 | CHO_cyOFFtgt |
|---|---|---|---|---|---|
| 335171 | 8.45E-08 | 1.24E-02 | 471.0 | 39.0 | 5.4 |
| 335232 | 2.46E-08 | 1.83E-02 | 288.0 | 42.5 | 5.3 |
| 335263 | 2.58E-06 | 3.85E-02 | 30.0 | 8.2 | 5.2 |

SEQUENCE LISTING

```
<160> NUMBER OF SEQ ID NOS: 87

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Asp Ser Ile Ser Ser Gly Asp Tyr Tyr
1               5                   10

<210> SEQ ID NO 2
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 2

Gly Asp Ser Ile Ser Ser Gly Gly Tyr Tyr
1               5                   10

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Ser Ile Ser Ser Gly Asp Tyr Tyr
1               5                   10

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Gly Ser Ile Ser Ser Ser Ser Tyr Tyr
1               5                   10

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Ser Phe Ser Gly Tyr Tyr
1               5

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Asp Ser Ile Ser Ser Ser Ser Tyr Tyr
1               5                   10

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 7

Gly Gly Ser Ile Thr Ser Ser Ser Tyr Tyr
1               5                   10

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gly Gly Ser Ile Ser Ser Ser Ser His Tyr
1               5                   10

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Gly Ser Ile Ile Ser Ser Ser Tyr Tyr
1               5                   10

<210> SEQ ID NO 10
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Ser Ile Asn Asp Asn Ser His Tyr
1               5                   10

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Tyr Tyr Ser Gly Val Thr
1               5

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ile Tyr Tyr Ser Gly Ala Thr
1               5
```

```
<210> SEQ ID NO 13
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ile Tyr Tyr Ser Gly Ser Thr
1               5

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ile Tyr Tyr Thr Gly Ser Thr
1               5

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Val Tyr Tyr Thr Gly Ala Thr
1               5

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ile His Tyr Ser Gly Ser Thr
1               5

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ile Tyr Tyr Ser Gly Ser Ala
1               5

<210> SEQ ID NO 18
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 18

Thr Arg Glu Asp Ser Ser Asn Trp Arg Ser
1               5                   10

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Thr Arg Asp Asp Ser Ser Asn Trp Arg Ser
1               5                   10

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Thr Arg Glu Asp Ser Ser Ser Trp Arg Ser
1               5                   10

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ala Arg Glu Asp Ser Ser Ser Trp Arg Ser
1               5                   10

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Lys Arg Asp Asp Ser Ser Asn Trp Arg Ser
1               5                   10

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 23

Ala Arg Asp Asp Ser Ser Asn Trp Arg Ser
1               5                   10

<210> SEQ ID NO 24
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Ser Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Glu Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115
```

```
<210> SEQ ID NO 26
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 27
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 28
<211> LENGTH: 118
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 28

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 29
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 30

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 31
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Gly Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 32
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
            85                  90                  95

Cys Thr Arg Glu Asp Ser Ser Trp Arg Ser Arg Gly Gln Gly Thr
            100                 105                 110

Leu Val Thr Val Ser Ser
            115

<210> SEQ ID NO 33
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Val Thr Tyr Tyr Asn Pro Ser
 50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Thr Arg Asp Asp Ser Ser Asn Trp Arg Ser Arg Gly Gln Gly Thr
            100                 105                 110

Leu Val Thr Val Ser Ser
            115

<210> SEQ ID NO 34
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Val Thr Tyr Tyr Asn Pro Ser
 50                  55                  60

```
Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
                100                 105                 110

Leu Val Thr Val Ser Ser
            115

<210> SEQ ID NO 35
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
                20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
        50                  55                  60

Leu Glu Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
                100                 105                 110

Leu Val Thr Val Ser Ser
            115

<210> SEQ ID NO 36
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
                20                  25                  30

Asp Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
        50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95
```

```
Cys Thr Arg Glu Asp Ser Ser Trp Arg Ser Arg Gly Gln Gly Thr
            100                 105                 110

Leu Val Thr Val Ser Ser
        115

<210> SEQ ID NO 37
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
 50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 38
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115
```

```
<210> SEQ ID NO 39
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 41
<211> LENGTH: 118
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
            85                  90                  95

Cys Thr Arg Glu Asp Ser Ser Asn Trp Arg Ser Arg Gly Gln Gly Thr
            100                 105                 110

Leu Val Thr Val Ser Ser
            115

<210> SEQ ID NO 42
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Tyr Tyr Asn Pro Ser
50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Thr Arg Asp Asp Ser Ser Asn Trp Arg Ser Arg Gly Gln Gly Thr
            100                 105                 110

Leu Val Thr Val Ser Ser
            115

<210> SEQ ID NO 43
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 43

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 44
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Glu Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
            35                  40                  45

Trp Ile Gly Asn Ile Tyr Tyr Ser Gly Ala Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 47
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
            20                  25                  30

Gly Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

```
Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 48
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
             20                  25                  30

Asp Tyr Tyr Trp Gly Trp Ile Arg His Pro Pro Gly Lys Gly Leu Glu
         35                  40                  45

Trp Ile Gly His Ile Tyr Tyr Ser Gly Ala Thr Tyr Tyr Asn Pro Ser
     50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 49
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Gly
             20                  25                  30

Asp Tyr Tyr Trp Gly Trp Ile Arg Gln Pro Pro Gly Lys Gly Leu Glu
         35                  40                  45

Trp Ile Gly Asn Ile Tyr Tyr Ser Gly Ala Thr Tyr Tyr Asn Pro Ser
     50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95
```

```
Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 50
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Asn Ile Tyr Tyr Ser Gly Ala Thr Tyr Tyr Asn Pro Ser
50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 51
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115
```

```
<210> SEQ ID NO 52
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Thr Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 54
<211> LENGTH: 118
<212> TYPE: PRT
<213> ORGANISM: Artificial Sequence
```

<220> FEATURE:
<221> NAME/KEY: source
<223> OTHER INFORMATION: /note="Description of Artificial Sequence:
    Synthetic polypeptide"

<400> SEQUENCE: 54

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
50                  55                  60

Leu Lys Asn Arg Val Thr Ile Ser Val Asp Thr Ser Arg Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
            115

<210> SEQ ID NO 55
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 55

Gln Leu Gln Leu Gln Glu Ser Gly Pro Gly Leu Val Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Gly Trp Ile Arg Gln Pro Pro Gly Lys Gly Leu Glu Trp Ile
        35                  40                  45

Gly His Ile Tyr Tyr Ser Gly Ala Thr Tyr Tyr Asn Pro Ser Leu Lys
    50                  55                  60

Asn Arg Val Thr Ile Ser Val Asp Thr Ser Arg Asn Gln Phe Ser Leu
65                  70                  75                  80

Asn Leu Ser Ser Val Thr Ala Ala Asp Thr Ala Val Tyr Tyr Cys Thr
                85                  90                  95

Arg Glu Asp Ser Ser Ser Trp Arg Ser Arg Gly Gln Gly Thr Leu Val
            100                 105                 110

Thr Val Ser Ser
            115

<210> SEQ ID NO 56
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 56

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Ala Tyr Tyr
            85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 57
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly His Ile Tyr Tyr Ser Gly Val Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 58
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

```
Ser Tyr Tyr Trp Gly Trp Ile Arg Gln Pro Pro Lys Gly Leu Glu
         35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Arg Asn Gln Phe
 65                  70                  75                  80

Ser Leu Asn Leu Ser Ser Val Thr Ala Ala Asp Thr Ala Val Tyr Tyr
             85                  90                  95

Cys Thr Arg Glu Asp Ser Ser Trp Arg Ser Arg Gly Gln Gly Thr
                100                 105                 110

Leu Val Thr Val Ser Ser
        115
```

<210> SEQ ID NO 59
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Ser
            20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Thr Arg Glu Asp Ser Ser Asn Trp Arg Ser Arg Gly Gln Gly Thr
                100                 105                 110

Leu Val Thr Val Ser Ser
        115
```

<210> SEQ ID NO 60
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Ser
 50                  55                  60
```

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Asp Ser Ser Trp Arg Ser Arg Gly Gln Gly Thr
            100                 105                 110

Leu Val Thr Val Ser Ser
        115
```

<210> SEQ ID NO 61
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ala Thr Tyr Tyr Asn Pro Ser
 50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Glu Asp Ser Ser Trp Arg Ser Arg Gly Gln Gly Thr
            100                 105                 110

Leu Val Thr Val Ser Ser
        115
```

<210> SEQ ID NO 62
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
 50                  55                  60

Leu Lys Asn Arg Val Thr Ile Ser Val Asp Ser Arg Asn Gln Phe
 65                  70                  75                  80

Ser Leu Asn Leu Ser Ser Val Thr Ala Ala Asp Thr Ala Val Tyr Tyr
                 85                  90                  95
```

```
Cys Thr Arg Glu Asp Ser Ser Trp Arg Ser Arg Gly Gln Gly Thr
                100                 105                 110

Leu Val Thr Val Ser Ser
        115

<210> SEQ ID NO 63
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
                100                 105                 110

Leu Val Thr Val Ser Ser
        115

<210> SEQ ID NO 64
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
                100                 105                 110

Leu Val Thr Val Ser Ser
        115
```

<210> SEQ ID NO 65
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Tyr Tyr Asn Pro Ser
50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Ser Trp Arg Ser Arg Gly Gln Gly Thr
            100                 105                 110

Leu Val Thr Val Ser Ser
        115

<210> SEQ ID NO 66
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 67
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 67

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 68
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 68

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Val Thr Tyr Tyr Asn Pro Ser
    50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 69
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 69

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 70
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Gln Leu Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
            100                 105                 110

Leu Val Thr Val Ser Ser
        115

<210> SEQ ID NO 71
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 72
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ala Thr Tyr Tyr Asn Pro Ser
 50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Met Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 73
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Val Thr Tyr Tyr Asn Pro Ser
 50                  55                  60

```
Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Thr Arg Glu Asp Ser Ser Trp Arg Ser Arg Gly Gln Gly Thr
            100                 105                 110

Leu Val Thr Val Ser Ser
            115

<210> SEQ ID NO 74
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Asp Ser Ile Ser Ser Gly
                 20                  25                  30

Asp Tyr Tyr Trp Gly Trp Ile Arg Gln Ser Pro Glu Lys Gly Leu Glu
             35                  40                  45

Trp Ile Gly His Ile Tyr Tyr Ser Gly Val Thr Tyr Tyr Asn Pro Ser
     50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Lys Arg Asp Asp Ser Ser Asn Trp Arg Ser Arg Gly Gln Gly Thr
            100                 105                 110

Leu Val Thr Val Ser Ser
            115

<210> SEQ ID NO 75
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
             35                  40                  45

Trp Ile Gly His Ile Tyr Tyr Ser Gly Ala Thr Tyr Tyr Asn Pro Ser
     50                  55                  60

Leu Lys Asn Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95
```

```
Cys Thr Arg Glu Asp Ser Ser Trp Arg Ser Arg Gly Gln Gly Thr
                100                 105                 110

Leu Val Thr Val Ser Ser
        115
```

<210> SEQ ID NO 76
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Val Tyr Tyr Thr Gly Ala Thr Tyr Tyr Asn Pro Ser
50                  55                  60

Leu Lys Asn Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
                100                 105                 110

Leu Val Thr Val Ser Ser
        115
```

<210> SEQ ID NO 77
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Phe Arg His Pro Pro Gly Lys Gly Leu Asp
        35                  40                  45

Trp Ile Gly Ser Ile His Tyr Ser Gly Ser Thr Tyr Tyr Asn Pro Ser
50                  55                  60

Leu Lys Ser Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
                100                 105                 110

Leu Val Thr Val Ser Ser
        115
```

```
<210> SEQ ID NO 78
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78
```

Gln Leu Gln Leu Gln Glu Ser Asp Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser His Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

```
<210> SEQ ID NO 79
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

```
<210> SEQ ID NO 80
<211> LENGTH: 118
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 80

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 81
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Ala Tyr Tyr His Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Asp Ser Ser Asn Trp Arg Ser Arg Gly Gln Gly Thr
            100                 105                 110

Leu Val Thr Val Ser Ser
        115

<210> SEQ ID NO 82
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Asp Asp Ser Ser Asn Trp Arg Ser Arg Gly Gln Gly Thr
            100                 105                 110

Leu Val Thr Val Ser Ser
        115

<210> SEQ ID NO 83
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Gly
            20                  25                  30

Asp Tyr Tyr Trp Gly Trp Ile Arg Gln Pro Pro Gly Lys Gly Leu Glu
        35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Ser
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Asn Trp Arg Ser Arg Gly Gln Gly Thr
            100                 105                 110

Leu Val Thr Val Ser Ser
        115

<210> SEQ ID NO 84
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Asp Asn
            20                  25                  30

```
Ser His Tyr Trp Gly Trp Ile Arg Gln Pro Pro Gly Lys Gly Leu Glu
            35                  40                  45

Trp Ile Gly His Ile Tyr Tyr Ser Gly Ala Thr Tyr Tyr Asn Pro Ser
    50                  55                  60

Leu Lys Asn Arg Val Thr Ile Ser Val Asp Thr Ser Arg Asn Gln Phe
65                  70                  75                  80

Ser Leu Asn Leu Ser Ser Val Thr Ala Ala Asp Thr Ala Val Tyr Tyr
                85                  90                  95

Cys Thr Arg Glu Asp Ser Ser Trp Arg Ser Arg Gly Gln Gly Thr
                100                 105                 110

Leu Val Thr Val Ser Ser
        115

<210> SEQ ID NO 85
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (5)..(5)
<223> OTHER INFORMATION: /replace="Thr" or "Ile" or "Asn"
<220> FEATURE:
<221> NAME/KEY: VARIANT
<222> LOCATION: (6)..(6)
<223> OTHER INFORMATION: /replace="Asp"
<220> FEATURE:
<221> NAME/KEY: VARIANT
<222> LOCATION: (7)..(7)
<223> OTHER INFORMATION: /replace="Ser" or "Asn"
<220> FEATURE:
<221> NAME/KEY: VARIANT
<222> LOCATION: (8)..(8)
<223> OTHER INFORMATION: /replace="Gly" or "Ser"
<220> FEATURE:
<221> NAME/KEY: VARIANT
<222> LOCATION: (9)..(9)
<223> OTHER INFORMATION: /replace="His"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 85

Gly Asp Ser Ile Ser Ser Gly Asp Tyr Tyr
1               5                   10

<210> SEQ ID NO 86
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Val"
```

```
<220> FEATURE:
<221> NAME/KEY: VARIANT
<222> LOCATION: (2)..(2)
<223> OTHER INFORMATION: /replace="His"
<220> FEATURE:
<221> NAME/KEY: VARIANT
<222> LOCATION: (4)..(4)
<223> OTHER INFORMATION: /replace="Thr"
<220> FEATURE:
<221> NAME/KEY: VARIANT
<222> LOCATION: (6)..(6)
<223> OTHER INFORMATION: /replace="Val" or "Ser"
<220> FEATURE:
<221> NAME/KEY: VARIANT
<222> LOCATION: (7)..(7)
<223> OTHER INFORMATION: /replace="Ala"
<220> FEATURE:
<221> NAME/KEY: SITE
<222> LOCATION: (1)..(7)
<223> OTHER INFORMATION: /note="Variant residues given in the sequence
      have no preference with respect to those in the annotations
      for variant positions"

<400> SEQUENCE: 86

Ile Tyr Tyr Ser Gly Ala Thr
1               5

<210> SEQ ID NO 87
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ala" or "Lys"
<220> FEATURE:
<221> NAME/KEY: VARIANT
<222> LOCATION: (3)..(3)
<223> OTHER INFORMATION: /replace="Glu"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: SITE
<222> LOCATION: (1)..(10)
<223> OTHER INFORMATION: /note="Variant residues given in the sequence
      have no preference with respect to those in the annotations
      for variant positions"

<400> SEQUENCE: 87

Thr Arg Asp Asp Ser Ser Asn Trp Arg Ser
1               5                   10
```

HEAVY CHAIN ANTIBODIES BINDING TO CD22

CROSS-REFERENCE TO RELATED APPLICATIONS

This application claims priority to the filing date of U.S. Provisional Patent Application No. 62/609,759, filed on Dec. 22, 2017, the disclosure of which application is herein incorporated by reference in its entirety.

SEQUENCE LISTING

The instant application contains a Sequence Listing which has been submitted electronically in ASCII format and is hereby incorporated by reference in its entirety. Said ASCII copy, created on Feb. 7, 2019, is named TNO-0009-WO_SL.txt and is 80,329 bytes in size.

FIELD OF THE INVENTION

The present invention concerns human heavy chain antibodies (e.g., UniAbs™) binding to CD22. The invention further concerns methods of making such antibodies, compositions, including pharmaceutical compositions, comprising such antibodies, and their use to treat B-cell disorders that are characterized by the expression of CD22.

BACKGROUND OF THE INVENTION

CD22

CD22, also known as SIGLEC-2 (UniProt P20273), is a cell-surface receptor that is expressed on mature B-cells. CD22 contains multiple Ig domains and is a member of the immunoglobulin superfamily. The extracellular domain of CD22 interacts with sialic acid moieties, including those present on the CD45 cell surface protein. CD22 is thought to function as an inhibitory receptor for B-cell receptor signaling. Along with CD20 and CD19, the restricted B-cell expression of CD22 makes it an attractive target for the therapeutic treatment of B-cell malignancies. Monoclonal antibodies specific to CD22 have been described in the literature (e.g., Jabbour, Elias, et al. "Monoclonal antibodies in acute lymphoblastic leukemia." *Blood* 125.26 (2015): 4010-4016) and have been used therapeutically as standard monoclonals (e.g., epratuzumab) as well as antibody-drug conjugates (inotuzumab ozogamicin). In addition, anti-CD22 chimeric antigen receptor T-cells have been used in the clinic to treat leukemia (Fry, Terry J., et al. "CD22-targeted CAR T cells induce remission in B-ALL that is naive or resistant to CD19-targeted CAR immunotherapy." *Nature medicine* (2017)).

Heavy Chain Antibodies

In a conventional IgG antibody, the association of the heavy chain and light chain is due in part to a hydrophobic interaction between the light chain constant region and the CH1 constant domain of the heavy chain There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs™). The UniAbs™ of Camelidae (*Camelus dromedarius, Camelus bactrianus, Lama glama, Lama guanaco, Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These UniAbs™ lack the first domain of the constant region (CH1) which is present in the genome, but is spliced out during mRNA processing. The absence of the CH1 domain explains the absence of the light chain in the UniAbs™, since this domain is the anchoring place for the constant domain of the light chain Such UniAbs™ naturally evolved to confer antigen-binding specificity and high affinity by three CDRs from conventional antibodies or fragments thereof (Muyldermans, 2001; *J Biotechnol* 74:277-302; Revets et al., 2005; *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The ability of heavy chain-only antibodies devoid of light chain to bind antigen was established in the 1960s (Jaton et al. (1968) *Biochemistry*, 7, 4185-4195). Heavy chain immunoglobulin physically separated from light chain retained 80% of antigen-binding activity relative to the tetrameric antibody. Sitia et al. (1990) *Cell*, 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Brüggemann et al., *Crit. Rev. Immunol.;* 2006, 26(5):377-90; and Zou et al., 2007, *J Exp Med;* 204(13): 3271-3283. The production of knockout rats via embryo microinjections of zinc-finger nucleases is described in Geurts et al., 2009, Science, 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domain are described, for example, in Iri-Sofia et al., 2011, *Experimental Cell Research* 317:2630-2641 and Jamnani et al., 2014, *Biochim Biophys Acta*, 1840:378-386.

SUMMARY OF THE INVENTION

Aspects of the invention relate to heavy chain antibodies, including but not limited to UniAbs™, with binding affinity to CD22. Further aspects of the invention relate to methods of making such antibodies, compositions comprising such antibodies, and their use in the treatment of B-cell disorders that are characterized by the expression of CD22.

In some embodiments, a heavy chain-only antibody binding to CD22 comprises a heavy chain variable region comprising: (a) a CDR1 having two or fewer substitutions in any of the amino acid sequences of SEQ ID NOs: 1 to 10; and/or (b) a CDR2 having two or fewer substitutions in any of the amino acid sequences of SEQ ID NOs: 11 to 17; and/or (c) a CDR3 having two or fewer substitutions in any of the amino acid sequences of SEQ ID NOs: 18 to 23. In some embodiments, the CDR1, CDR2, and CDR3 sequences are present in a human framework. In some embodiments, a heavy chain-only antibody further comprises a heavy chain constant region sequence in the absence of a CH1 sequence.

In some embodiments, a heavy chain-only antibody comprises: (a) a CDR1 sequence selected from the group consisting of SEQ ID NOs: 1 to 10; and/or (b) a CDR2 sequence selected from the group consisting of SEQ ID NOs: 11 to 17; and/or (c) a CDR3 sequence selected from the group consisting of SEQ ID NOs: 18 to 23. In some embodiments, a heavy chain-only antibody comprises: (a) a CDR1 sequence selected from the group consisting of SEQ ID NOs: 1 to 10; and (b) a CDR2 sequence selected from the group consisting of SEQ ID NOs: 11 to 17; and (c) a CDR3 sequence selected from the group consisting of SEQ ID NOs: 18 to 23.

In some embodiments, a heavy chain-only antibody comprises: (a) a CDR1 sequence of SEQ ID NO: 1, a CDR2 sequence of SEQ ID NO: 11, and a CDR3 sequence of SEQ ID NO: 18; or (b) a CDR1 sequence of SEQ ID NO: 1, a CDR2 sequence of SEQ ID NO: 12, and a CDR3 sequence of SEQ ID NO: 19; or (c) a CDR1 sequence of SEQ ID NO: 1, a CDR2 sequence of SEQ ID NO: 12, and a CDR3 sequence of SEQ ID NO: 20. In some embodiments, a heavy chain-only antibody comprises a heavy chain variable region having at least 95% sequence identity to any of the sequences of SEQ ID NOs: 24 to 84. In some embodiments, a heavy chain-only antibody comprises a heavy chain variable region sequence selected from the group consisting of SEQ ID NOs: 24 to 84. In some embodiments, a heavy chain-only antibody comprises a heavy chain variable region sequence of SEQ ID NO: 24.

In some embodiments, a heavy chain-only antibody binding to CD22 comprises a heavy chain variable region comprising a heavy chain variable comprising (a) a CDR1 sequence of the formula:

$$G\ X_1\ S\ I\ X_2\ X_3\ X_4\ X_5\ X_6\ Y \quad \text{(SEQ ID NO: 85)}$$

where $X_1$ is D or G; $X_2$ is S, T, I or N; $X_3$ is S or D; $X_4$ is G, S or N; $X_5$ is D, G or S; and $X_6$ is Y or H; and (b) a CDR2 sequence of the formula:

$$X_7\ X_8\ Y\ X_9\ G\ X_{10}\ X_{11} \quad \text{(SEQ ID NO: 86)}$$

where $X_7$ is I or V; $X_8$ is Y or H; $X_9$ is S or T; $X_{10}$ is A, V or S; and $X_{11}$ is T or A; and (c) a CDR3 sequence of the formula:

$$X_{12}\ R\ X_{13}\ D\ S\ S\ X_{14}\ W\ R\ S \quad \text{(SEQ ID NO: 87)}$$

where $X_{12}$ is T, A or K; $X_{13}$ is D or E; and $X_{14}$ is N or S.

In some embodiments, a heavy chain-only antibody binding to CD22 comprises a heavy chain variable region comprising CDR1, CDR2 and CDR3 sequences in a human VH framework wherein the CDR sequences are a sequence having two or fewer substitutions in a CDR sequence selected from the group consisting of SEQ ID NOs:1-23.

In some embodiments, a heavy chain-only antibody comprises a heavy chain variable region comprising CDR1, CDR2 and CDR3 sequences in a human VH framework wherein the CDR sequences are selected from the group consisting of SEQ ID NOs:1-23.

In some embodiments, a heavy chain-only antibody binding to CD22 comprises a heavy chain variable region comprising: (a) a CDR1 sequence of SEQ ID NO: 1, a CDR2 sequence of SEQ ID NO: 11, and a CDR3 sequence of SEQ ID NO: 18; or (b) a CDR1 sequence of SEQ ID NO: 1, a CDR2 sequence of SEQ ID NO: 12, and a CDR3 sequence of SEQ ID NO: 19; or (c) a CDR1 sequence of SEQ ID NO: 1, a CDR2 sequence of SEQ ID NO: 12, and a CDR3 sequence of SEQ ID NO: 20, in a human VH framework.

In some embodiments, a heavy chain-only antibody is multi-specific. In some embodiments, a heavy chain-only antibody is bispecific. In some embodiments, a heavy chain-only antibody has binding affinity to two different CD22 proteins. In some embodiments, a heavy chain-only antibody has binding affinity to two different epitopes on the same CD22 protein. In some embodiments, a heavy chain-only antibody has binding affinity to an effector cell. In some embodiments, a heavy chain-only antibody has binding affinity to a T-cell antigen. In some embodiments, a heavy chain-only antibody has binding affinity to CD3. In some embodiments, a heavy chain-only antibody is in a CAR-T format.

Aspects of the invention relate to pharmaceutical compositions comprising a heavy chain-only antibody described herein.

Aspects of the invention relate to methods for the treatment of a B-cell disorder characterized by expression of CD22 comprising administering to a subject with said disorder an antibody or a pharmaceutical composition described herein. In certain other aspects, the invention relates to uses of an antibody described herein, in the preparation of a medicament for the treatment of a B-cell disorder characterized by expression of CD22. In yet other aspects, the invention relates to an antibody described herein for use in the treatment of a B-cell disorder characterized by expression of CD22. With respect to these aspects, and in some embodiments, the disorder is diffuse large B cell lymphoma (DLBCL). In some embodiments, the disorder is non-Hodgkin's lymphoma (NHL). In some embodiments, the disorder is systemic lupus erythematosus (SLE). In some embodiments, the disorder is rheumatoid arthritis (RA). In some embodiments, the disorder is multiple sclerosis (MS).

Aspects of the invention relate to polynucleotides encoding an antibody described herein, vectors comprising such polynucleotides, and cells comprising such vectors.

Aspects of the invention relate to methods of producing an antibody described herein, comprising growing a cell described herein under conditions permissive for expression of the antibody, and isolating the antibody from the cell.

Aspects of the invention relate to methods of making an antibody described herein, comprising immunizing a UniRat animal with CD22 and identifying CD22-binding heavy chain sequences.

These and further aspects will be further explained in the rest of the disclosure, including the Examples.

BRIEF DESCRIPTION OF THE DRAWINGS

FIG. 1 shows anti-CD22 heavy chain antibody unique CDR amino acid sequences.

FIG. 2 shows anti-CD22 heavy chain antibody variable domain amino acid sequences.

FIG. 3 shows anti-CD22 heavy chain antibody CDR1, CDR2 and CDR3 amino acid sequences.

FIG. 4 shows anti-CD22 heavy chain antibody biological activities.

DETAILED DESCRIPTION OF THE PREFERRED EMBODIMENTS

Figure 5A:
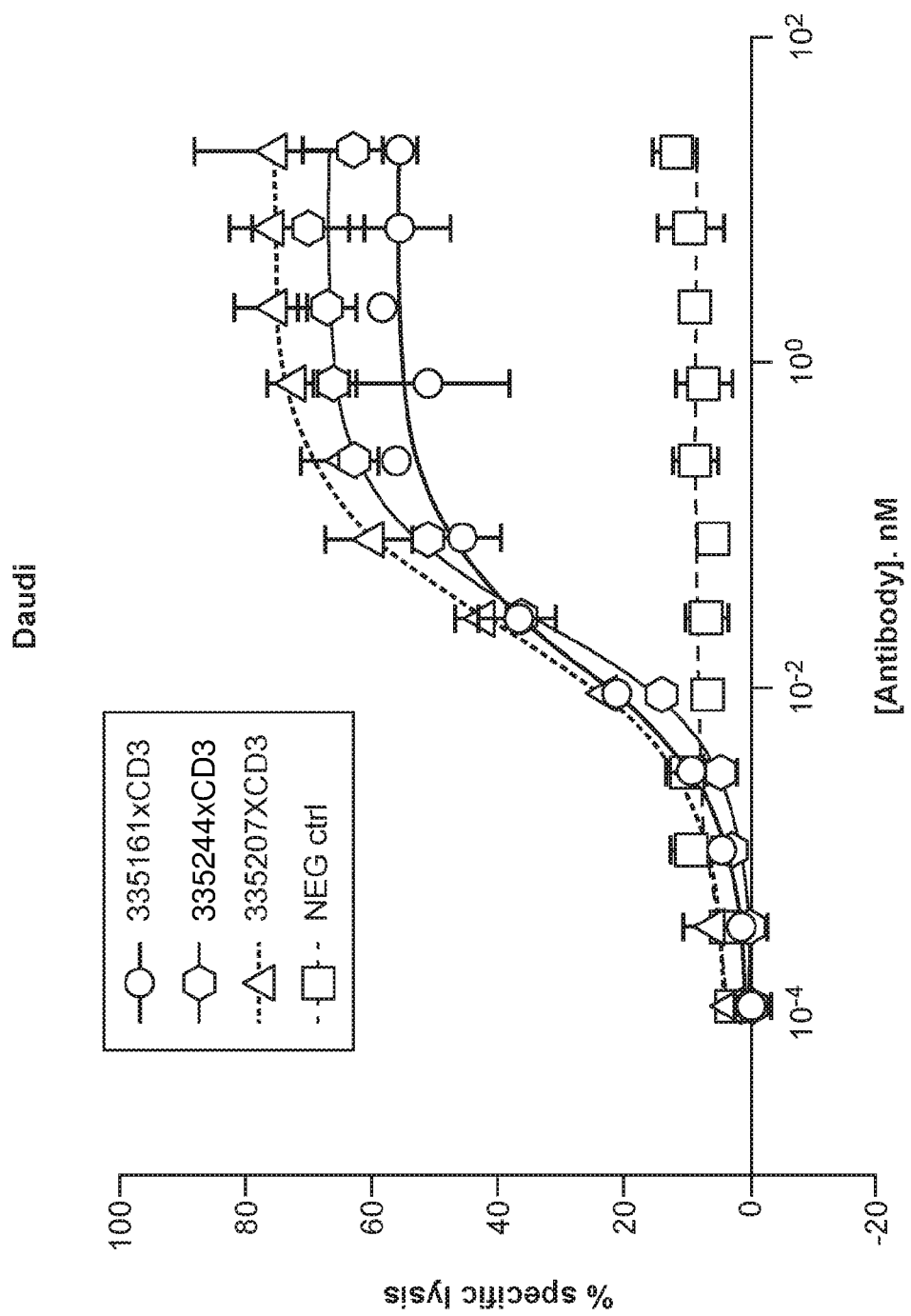
FIG. 5A is a graph depicting percent specific lysis as a function of antibody concentration for Daudi cells.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies in accordance with the present invention can be made by the hybridoma method first described by Kohler et al. (1975) *Nature* 256:495, an can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" residues 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Exemplary CDR designations are shown herein, however one of skill in the art will understand that a number of definitions of the CDRs are commonly in use, including the Kabat definition (see "Zhao et al. A germline knowledge based computational approach for determining antibody complementarity determining regions." *Mol Immunol.* 2010; 47:694-700), which is based on sequence variability and is the most commonly used. The Chothia definition is based on the location of the structural loop regions (Chothia et al. "Conformations of immunoglobulin hypervariable regions." *Nature.* 1989; 342:877-883). Alternative CDR definitions of interest include, without limitation, those disclosed by Honegger, "Yet another numbering scheme for immunoglobulin variable domains: an automatic modeling and analysis tool." *J Mol Biol.* 2001; 309:657-670; Ofran et al. "Automated identification of complementarity determining regions (CDRs) reveals peculiar characteristics of CDRs and B cell epitopes." *J Immunol.* 2008; 181:6230-6235; Almagro "Identification of differences in the specificity-determining residues of antibodies that recognize antigens of different size: implications for the rational design of antibody repertoires." *J Mol Recognit.* 2004; 17:132-143; and Padlan et al. "Identification of specificity-determining residues in antibodies." *Faseb J.* 1995; 9:133-139., each of which is herein specifically incorporated by reference.

The terms "heavy chain-only antibody," and "heavy chain antibody" are used interchangeably herein and refer, in the broadest sense, to antibodies lacking the light chain of a conventional antibody. The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs™). In one embodiment, the heavy chain-only antibody is composed of the variable region antigen-binding domain composed of framework 1, CDR1, framework 2, CDR2, framework 3, CDR3, and framework 4. In another embodiment, the heavy chain-only antibody is composed of an antigen-binding domain, at least part of a hinge region and CH2 and CH3 domains. In another embodiment, the heavy chain-only antibody is composed of an antigen-binding domain, at least part of a hinge region and a CH2 domain. In a further embodiment, the heavy chain-only antibody is composed of an antigen-binding domain, at least part of a hinge region and a CH3 domain. Heavy chain-only antibodies in which the CH2 and/or CH3 domain is truncated are also included herein. In a further embodiment the heavy chain is composed of an antigen binding domain, and at least one CH (CH1, CH2, CH3, or CH4) domain but no hinge region. The heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype. In one embodiment, the heavy chain-only antibodies herein are used as a binding (targeting) domain of a chimeric antigen receptor (CAR). The definition specifically includes human heavy chain-only antibodies produced by human immunoglobulin transgenic rats (UniRat™), called UniAbs™. The variable regions (VH) of UniAbs™ are called UniDabs™, and are versatile building blocks that can be linked to Fc regions or serum albumin for the development of novel therapeutics with multi-specificity, increased potency and extended half-life. Since the homodimeric UniAbs™ lack a light chain and thus a VL domain, the antigen is recognized by one single domain, i.e., the variable domain of the heavy chain of a heavy-chain antibody (VH).

The terms "CD22" and "cluster of differentiation-22" as used herein refer to a molecule belonging to the SIGLEC family of lectins, found on the surface of mature B cells, and to a lesser extent on some immature B cells. The term "CD22" includes a CD22 protein of any human and non-human animal species, and specifically includes human CD22 as well as CD22 of non-human mammals.

The term "human CD22" as used herein includes any variants, isoforms and species homologs of human CD22 (UniProt P20273), regardless of its source or mode of preparation. Thus, "human CD22" includes human CD22 naturally expressed by cells and CD22 expressed on cells transfected with the human CD22 gene.

The terms "anti-CD22 heavy chain-only antibody," "CD22 heavy chain-only antibody," "anti-CD22 heavy chain antibody" and "CD22 heavy chain antibody" are used herein interchangeably to refer to a heavy chain-only antibody as hereinabove defined, immunospecifically binding to CD22, including human CD22, as hereinabove defined. The definition includes, without limitation, human heavy chain antibodies produced by transgenic animals, such as transgenic rats or transgenic mice expressing human immunoglobulin, including UniRats™ producing human anti-CD22 UniAb™ antibodies, as hereinabove defined.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. "Multi-specific" antibodies specifically include antibodies comprising a combination of different binding entities as well as antibodies comprising more than one of the same binding entity. The terms "multi-specific antibody," "multi-specific heavy chain-only antibody," "multi-specific heavy chain antibody," and "multi-specific UniAb™" are used herein in the broadest sense and cover all antibodies with more than one binding specificity. The multi-specific heavy chain anti-CD22 antibodies of the present invention specifically include antibodies immuno-specifically binding to more than one non-overlapping epitopes on a CD22 protein, such as a human CD22.

An "epitope" is the site on the surface of an antigen molecule to which a single antibody molecule binds. Generally an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present invention specifically includes anti-CD22 heavy chain antibodies with polyepitopic specificities, i.e. anti-CD22 heavy chain antibodies binding to two or more non-overlapping epitopes on a CD22 protein, such as a human CD22. The term "non-overlapping epitope(s)" or "non-competitive epitope(s)" of an antigen is defined herein to mean epitope(s) that are recognized by one member of a pair of antigen-specific antibodies but not the other member. Pairs of antibodies, or antigen-binding regions targeting the same antigen on a multi-specific antibody, recognizing non-overlapping epitopes do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent.

A large variety of methods and protein configurations are known and used for the preparation of bispecific monoclonal antibodies (BsMAB), tri-specific antibodies, and the like.

The term "bispecific three-chain antibody like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain-only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain Parts of such variable region may be encoded by $V_H$ and/or $V_L$ gene segments, D and $J_H$ gene segments, or $J_L$ gene segments. The variable region may be encoded by rearranged $V_H DJ_H$, $V_L DJ_H$, $V_H J_L$, or $V_L J_L$ gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T cell to create a chimeric antigen receptors (CAR). (*J Natl Cancer Inst,* 2015; 108(7):dvj439; and Jackson et al., *Nature Reviews Clinical Oncology,* 2016; 13:370-383.)

The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T cell receptors or FcRs and perform effector functions. Preferably, the cells express at least FcγRIII and perform ADCC effector function. Examples of human leukocytes which mediate ADCC include natural killer (NK) cells, monocytes, cytotoxic T cells and neutrophils; with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B cells and T cells including cytolytic T cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, Calif.) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen*, 12(8), 791-800, 2009).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "B-cell neoplasms" or "mature B-cell neoplasms" in the context of the present invention include small lymphocytic lymphoma, B-cell prolymphocytic lymphoma, B-cell chronic lymphocytic leukemia, mantle cell lymphoma, Burkitt's lymphoma, follicular lymphoma, diffuse large B-cell lymphoma (DLBCL), multiple myeloma, lymphoplasmacytic lymphoma, splenic marginal zone lymphoma, plasma cell neoplasms, such as plasma cell myeloma, plasmacytoma, monoclonal immunoglobulin deposition disease, heavy chain disease, MALT lymphoma, nodal marginal B cell lymphoma, intravascular large B cell lymphoma, primary effusion lymphoma, lymphomatoid granulomatosis, non-Hodgkins lymphoma, Hodgkins lymphoma, hairy cell leukemia, primary effusion lymphoma and AIDS-related non-Hodgkins lymphoma.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomeriation), clipping/hydrolysis/fragmentation (e.g., hinge region fragmentation), succinimide formation, unpaired cysteine(s), N-terminal extension, C-terminal processing, glycosylation differences, etc.

II. Detailed Description

Anti-CD22 Antibodies

The present invention provides a family of closely related heavy chain-only antibodies that bind to human CD22. The antibodies of this family comprise a set of CDR sequences as defined herein and shown in FIG. 1, and are exemplified by the provided heavy chain variable region (VH) sequences of SEQ ID NOs: 24 to 84 set forth in FIG. 2. The families of antibodies provide a number of benefits that contribute to utility as clinically therapeutic agent(s). The antibodies include members with a range of binding affinities, allowing the selection of a specific sequence with a desired binding affinity.

Figure 5B:
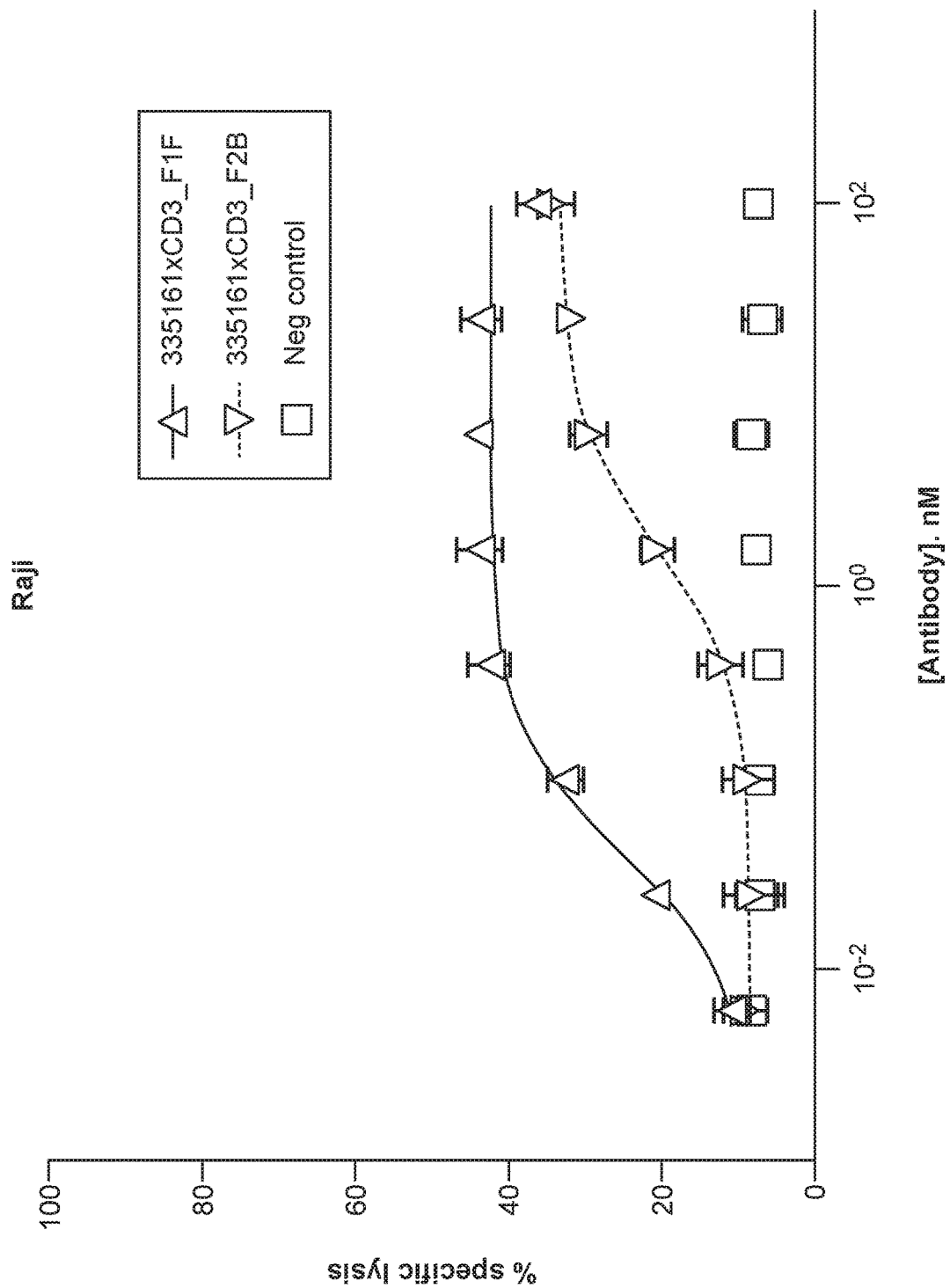
FIG. 5B is a graph depicting percent specific lysis as a function of antibody concentration for Raji cells.

A suitable antibody may be selected from those provided herein for development and therapeutic or other use, including, without limitation, use as a bispecific antibody, e.g., as shown in FIG. 5B, or tri-specific antibody, or part of a CAR-T structure.

Determination of affinity for a candidate protein can be performed using methods known in the art, such as Biacore measurements. Members of the antibody family may have an affinity for CD22 with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a CD22 biological activity, including in vitro assays, pre-clinical models, and clinical trials, as well as assessment of potential toxicity.

Members of the antibody family herein are not cross-reactive with the CD22 protein of *Cynomolgus* macaque, but can be engineered to provide cross-reactivity with theCD22 protein of *Cynomolgus* macaque, or with the CD22 of any other animal species, if desired.

The family of CD22-specific antibodies herein comprises a VH domain, comprising CDR1, CDR2 and CDR3 sequences in a human VH framework. The CDR sequences may be situated, as an example, in the region of around amino acid residues 26-35; 53-59; and 98-117 for CDR1, CDR2 and CDR3, respectively, of the provided exemplary variable region sequences set forth in SEQ ID NOs: 24 to 84. It will be understood by one of ordinary skill in the art that the CDR sequences may be in different positions if a different framework sequence is selected, although generally the order of the sequences will remain the same.

The CDR1, CDR2, and CDR3 sequences of the anti-CD22 antibodies of the present invention may be encompassed by the following structural formulas, where an X indicates a variable amino acid, which may be specific amino acids as indicated below.

CDR1

G $X_1$ S I $X_2$ $X_3$ $X_4$ $X_5$ $X_6$ Y   (SEQ ID NO: 85)

where $X_1$ is D or G;

$X_2$ is S, T, I or N;

$X_3$ is S or D;

$X_4$ is G, S or N;

$X_5$ is D, G or S; and $X_6$ is Y or H.

CDR2

$X_7 X_8 Y X_9 G X_{10} X_{11}$ (SEQ ID NO: 86)

where $X_7$ is I or V;
$X_8$ is Y or H;
$X_9$ is S or T;
$X_{10}$ is A, V or S; and
$X_{11}$ is T or A.

CDR3

$X_{12} R X_{13} D S S X_{14} W R S$ (SEQ ID NO: 87)

where $X_{12}$ is T, A or K;
$X_{13}$ is D or E; and
$X_{14}$ is N or S.

Representative CDR1, CDR2 and CDR3 sequences are shown in FIG. 1 and FIG. 3.

In some embodiments, an anti-CD22 heavy chain-only antibody of the invention comprises a CDR1 sequence of any one of SEQ ID NOs: 1-10. In a particular embodiment, the CDR1 sequence is SEQ ID NO: 1.

In some embodiments, an anti-CD22 heavy chain-only antibody of the invention comprises a CDR2 sequence of any one of SEQ ID NOs: 11-17. In a particular embodiment, the CDR2 sequence is SEQ ID NO: 11.

In some embodiments, an anti-CD22 heavy chain-only antibody of the invention comprises a CDR3 sequence of any one of SEQ ID NOs: 18-23. In a particular embodiment, the CDR2 sequence is SEQ ID NO: 18.

In a further embodiment, an anti-CD22 heavy chain-only antibody of the invention comprises the CDR1 sequence of SEQ ID NO:1; the CDR2 sequence of SEQ ID NO: 11; and the CDR3 sequence of SEQ ID NO: 18.

In further embodiments, an anti-CD22 heavy chain-only antibody of the invention comprises any of the heavy chain variable region amino acid sequences of SEQ ID NOs: 24 to 84 (FIG. 2).

In a still further embodiment, an anti-CD22 heavy chain-only antibody of the present invention comprises the heavy chain variable region sequence of SEQ ID NO: 24.

In some embodiments, a CDR sequence in an anti-CD22 heavy chain-only antibody of the invention differs one or two amino acid substitutions relative to a CDR1, CDR2 and/or CDR3 sequence or set of CDR1, CDR2 and CDR3 sequences in any one of SEQ ID NOs:1 to 23 (FIG. 1). In some embodiments, said amino acid substitution(s) are one or two of amino acid positions 4-6 of CDR1, and/or one or two of the amino acid positions of 2, 4-7 of CDR2, and/or one or two of the amino acid positions 5 and 12 of CDR3, relative to the formulas provided above. In some embodiments, the heavy chain-only anti-CD22 antibodies herein will comprise a heavy chain variable region sequence with at least about 85% identity, at least 90% identity, at least 95% identity, at least 98% identify, or at least 99% identity to any of the heavy chain variable region sequences of SEQ ID NOs: 24 to 84 (shown in FIG. 2).

In some embodiments, bispecific or multispecific antibodies are provided, which may have any of the configurations discussed herein, including, without limitation, a bispecific three-chain antibody like molecule. In some embodiments, a bispecific antibody can comprise at least one heavy chain variable region having binding specificity for CD22, and at least one heavy chain variable region having binding specificity for a protein other than CD22. In some embodiments, a bispecific antibody can comprise a heavy chain/light chain pair that has binding specificity for a first antigen, and a heavy chain from a heavy chain-only antibody, comprising an Fc portion comprising CH2 and/or CH3 and/or CH4 domains, in the absence of a CH1 domain, and an antigen binding domain that binds an epitope of a second antigen or a different epitope of the first antigen. In one particular embodiment, a bispecific antibody comprises a heavy chain/light chain pair that has binding specificity for an antigen on an effector cell (e.g., a CD3 protein on a T cell), and a heavy chain from a heavy chain-only antibody comprising an antigen-binding domain that has binding specificity for CD22.

In some embodiments, where a protein of the invention is a bispecific antibody, one arm of the antibody (one binding moiety) is specific for human CD22, while the other arm may be specific for target cells, tumor-associated antigens, targeting antigens, e.g., integrins, etc., pathogen antigens, checkpoint proteins, and the like. Target cells specifically include cancer cells, including, without limitation, cells from hematologic tumors, e.g. B-cell tumors, as discussed below.

Various formats of bispecific antibodies are within the ambit of the invention, including, without limitation, single chain polypeptides, two chain polypeptides, three chain polypeptides, four chain polypeptides, and multiples thereof. The bispecific antibodies herein specifically include T cell bispecific antibodies binding to CD22, which is selectively expressed on mature B-cells, and CD3 (anti-CD22×anti-CD3 antibodies). Such antibodies induce potent T cell mediated killing of cells expressing CD22.

Preparation of Anti-CD22 Heavy Chain Antibodies

The heavy chain antibodies of the present invention can be prepared by methods known in the art. In a preferred embodiment, the heavy chain antibodies herein are produced by transgenic animals, including transgenic mice and rats, preferably rats, in which the endogenous immunoglobulin genes are knocked out or disabled. In a preferred embodiment, the heavy chain antibodies herein are produced in UniRat™. UniRat™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety technologies, in UniRat™ the zinc-finger (endo) nuclease (ZNF) technology was used to inactivate the endogenous rat heavy chain J-locus, light chain Cκ locus and light chain Cλ locus. ZNF constructs for microinjection into oocytes can produce IgH and IgL knock out (KO) lines. For details see, e.g., Geurts et al., 2009, Science 325:433. Characterization of Ig heavy chain knockout rats has been reported by Menoret et al., 2010, Eur. J. Immunol. 40:2932-2941. Advantages of the ZNF technology are that non-homologous end joining to silence a gene or locus via deletions up to several kb can also provide a target site for homologous integration (Cui et al., 2011, Nat Biotechnol 29:64-67). Human heavy chain antibodies produced in UniRat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, rat can also be used, rats and mice being preferred. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), *E. coli* or yeast.

Domains of heavy chain-only antibodies combine advantages of antibodies and small molecule drugs: can be mono- or multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost effective manner.

In a particular embodiment, the heavy chain antibodies of the present invention, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. The substituted amino acid residue preferably is charged, and more preferably is positively charged, such as lysine (Lys, K), arginine (Arg, R) or histidine (His, H), preferably arginine (R). In a preferred embodiment the heavy chain-only antibodies derived from the transgenic animals contain a Trp to Arg mutation at position 101. The resultant HCAbs preferably have high antigen-binding affinity and solubility under physiological conditions in the absence of aggregation.

As part of the present invention, human IgG anti-CD22 heavy chain antibodies with unique sequences from Uni-Rat™ animals (UniAb™) were identified that bind human CD22 in ELISA (recombinant CD22 extracellular domain) protein and cell-binding assays. The identified heavy chain variable region (VH) sequences (see FIG. 2) are positive for human CD22 protein binding and/or for binding to CD22+ cells, and are all are negative for binding to cells that do not express CD22.

The antibodies described herein bind CD22-positive Burkitt's lymphoma cell line Daudi (ATCC® CCL-213™), and some are cross-reactive with the CD22 protein of *Cynomolgus macaque*. In addition, they can be engineered to provide cross-reactivity with the CD22 protein of any animal species, if desired.

The anti-CD22 heavy chain antibodies, such as UniAbs™ herein may have an affinity for CD22 with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a CD22 biological activity, including in vitro assays, pre-clinical models, and clinical trials, as well as assessment of potential toxicity.

Heavy chain antibodies binding to non-overlapping epitopes on a CD22 protein, e.g., UniAbs™ can be identified by competition binding assays, such as enzyme-linked immunoassays (ELISA assays) or flow cytometric competitive binding assays. nFor example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn XPR36 (BioRad, Inc), Biacore 2000 and Biacore T200 (GE Healthcare Life Sciences), and MX96 SPR imager (Ibis technologies B.V.), as well as on biolayer interferometry platforms, such as Octet Red384 and Octet HTX (ForteBio, Pall Inc). For further details see the examples herein.

Typically, an antibody "competes" with a reference antibody if it causes about 15-100% reduction in the binding of the reference antibody to the target antigen, as determined by standard techniques, such as by the competition binding assays described above. In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, at least about 95% or higher.

Pharmaceutical Compositions, Uses and Methods of Treatment

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

In one embodiment, a pharmaceutical composition comprises a heavy chain antibody (e.g., UniAb™) that binds to CD22. In another embodiment, a pharmaceutical composition comprises a multi-specific (including bispecific) heavy chain antibody (e.g., UniAb™) with binding specificity for two or more non-overlapping epitopes on a CD22 protein. In a preferred embodiment, a pharmaceutical composition comprises a multi-specific (including bispecific) heavy chain antibody (e.g., UniAb™) with binding specificity to CD22 and with binding specificity to a binding target on an effector cell (e.g., a binding target on a T cell, such as, e.g., a CD3 protein on a T cell).

Pharmaceutical composition of the antibodies used in accordance with the present invention are prepared for storage by mixing proteins having the desired degree of purity with optional pharmaceutically acceptable carriers, excipients or stabilizers (see, e.g. Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol;

resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively antibodies can be in lyophilized form for constitution with a suitable vehicle, e.g., sterile pyrogen-free water, before use.

Antibody formulations are disclosed, for example, in U.S. Pat. No. 9,034,324. Similar formulations can be used for the heavy chain antibodies, including UniAbs™, of the present invention. Subcutaneous antibody formulations are described, for example, in US20160355591 and US20160166689.

Methods of Use

The heavy chain-only anti-CD22 antibodies, multi-specific antibodies, and pharmaceutical compositions described herein can be used for the treatment of diseases and conditions characterized by the expression of CD22, including, without limitation, the conditions and diseases described further herein. Aspects of the invention also relate to uses of an antibody described herein, in the preparation of a medicament for the treatment of a B-cell disorder characterized by expression of CD22. Aspects of the invention also relate to an antibody described herein for use in the treatment of a B-cell disorder characterized by expression of CD22.

CD22 is a 135-kDa type I transmembrane protein that is expressed at low levels on pre- and immature B cells, maximally on mature B cells, and ultimately downregulated on plasma cells. (E.g., Walker et al., Immunology, 2008 March; 123(3) 314-25). CD22 is strongly expressed in follicular (primary and secondary B cell zones), mantle, and marginal zone B cells, and has been reported to be present in 60% to 80% of samples from patients with B cell malignancies (Alderson et al., Clin. Cancer Res 2009; 15(3) Feb. 11, 2009). Due to its observed expression in a number of hematological malignancies, CD22 is a promising target for antibody-based therapeutics.

In one aspect, the CD22 heavy chain antibodies (e.g., UniAbs™) and pharmaceutical compositions herein can be used to treat hematological malignancies characterized by the expression of CD22, including, without limitation, diffuse large B cell lymphoma (DLBCL), non-Hodgkin's lymphoma, B-cell chronic lymphocylic leukemia (CLL), and B-cell acute lymphoblastic leukemia (ALL).

Diffuse large B cell lymphoma (DLBCL or DLBL) is the most common form of non-Hodgkin's lymphoma among adults (Blood 1997 89 (11): 3909-18), with an estimated annual incidence of 7 to 8 cases per 100,000 people per year in the US and the UK. It is characterized as an aggressive cancer that can arise in virtually any part of the body. The causes of DLBCL are not well understood, and it can arise from normal B cells as well as malignant transformation of other types of lymphoma or leukemia cells. Treatment approaches generally involve chemotherapy and radiation, and have resulted in an overall five-year survival rate average of approximately 58% for adults. Although some monoclonal antibodies have shown promise for treating DLBCL, consistent clinical efficacy has not yet been conclusively demonstrated. There is therefore a great need for new therapies, including immunotherapies, for DLBCL.

In another aspect, the CD22 heavy chain antibodies (e.g., UniAbs™) and pharmaceutical compositions herein can be used to treat autoimmune disorders characterized by pathogenic B-cells that express CD22, including, without limitation, systemic lupus erythematosus (SLE), rheumatoid arthritis (RA), and multiple sclerosis (MS).

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g. lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e g, by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g. a chemotherapeutic drug, etc. Kits typically contain a label indicating the intended use of the contents of the kit. The term "label" as used herein includes any writing, or recorded material supplied on or with a kit, or which otherwise accompanies a kit.

The invention now being fully described, it will be apparent to one of ordinary skill in the art that various changes and modifications can be made without departing from the spirit or scope of the invention.

EXAMPLES

Materials and Methods
CD22 Protein Binding

The kinetic binding experiments to determine the antigen-antibody affinities were performed on the Octet QK-384 system (ForteBio) using bilayer interferometry. Anti-human IgG Fc Capture (AHC) biosensors (Forte Bio, Part No: 18-5064) were hydrated in assay buffer (lx PBS, 0.1% BSA, 0.02% Tween-20, pH 7.2) and preconditioned in 100 mM Glycine pH 1.5. A baseline was established in the assay buffer for 120 seconds. AHC biosensors were then immobilized with UniAbs™ at a concentration of 5 µg/mL for 120 seconds. Another baseline (120 seconds) was established in the assay buffer. Next, they were then dipped into a 7-point, 1:2 dilution series of the human CD22 protein in the assay buffer, starting from 250 nM. The last well of the analyte column contained only assay buffer to test for non-specific binding between the buffer and the loaded biosensors, and was used as a reference well. Association was observed for 600 seconds, followed by dissociation for 900 seconds. Data analysis was performed using Octet Data Analysis v9.0 (ForteBio). Binding kinetics were analyzed using a standard 1:1 binding model.

CD22 Cell Binding

Binding to CD22 positive cells was assessed by flow cytometry (Guava easyCyte 8HT, EMD Millipore) using the Daudi cell line (ATCC). Briefly, 100,000 target cells were stained with a dilution series of purified UniAbs™ for 30 minutes at 4° C. Following incubation, the cells were washed twice with flow cytometry buffer (1×PBS, 1% BSA, 0.1% $NaN_3$) and stained with goat F(ab')2 anti-human IgG conjugated to R-phycoerythrin (PE) (Southern Biotech, cat. #2042-09) to detect cell-bound antibodies. After a 20-minute incubation at 4° C., the cells were washed twice with flow cytometry buffer and then mean fluorescence intensity (MFI) was measured by flow cytometry. EC50 values were calculated using GraphPad Prism 7. Binding to *cynomolgus* CD22 positive cells was determined using the same protocol with the following modifications: the target cells were from CHO cells stably transfected to express the extracellular domain of *cynomolgus* CD22 and each antibody was tested at a single concentration (~1.7 µg/mL) so EC50 values were not calculated.

Example 1: Genetically Engineered Rats Expressing Heavy Chain-Only Antibodies A 'human—rat' IgH locus was constructed and assembled in several parts. This involved the modification and joining of rat C region genes downstream of human $J_H$s and subsequently, the upstream addition of the human $V_H$6-D-segment region. Two BACs with separate clusters of human $V_H$ genes [BAC6 and BAC3] were then co-injected with the BAC termed Georg, encoding the assembled and modified region comprising human $V_H$6, all Ds, all $J_H$s, and modified rat Cγ2a/1/2b ($\Delta C_H 1$).

Transgenic rats carrying artificial heavy chain immunoglobulin loci in unrearranged configuration were generated. The IgG2a($\Delta C_H 1$)., IgG1($\Delta C_H 1$)., IgG2b($\Delta C_H 1$) genes lacked the $C_H 1$ segment. The constant region genes IgE, IgA and 3' enhancer were included in Georg BAC. RT-PCR and serum analysis (ELISA) of transgenic rats revealed productive rearrangement of transgenic immunoglobulin loci and expression of heavy chain-only antibodies of various isotypes in serum. Transgenic rats were cross-bred with rats with mutated endogenous heavy chain and light chain loci previously described in US patent publication 2009/0098134 A1. Analysis of such animals demonstrated inactivation of rat immunoglobulin heavy and light chain expression and high level expression of heavy chain antibodies with variable regions encoded by human V, D, and J genes. Immunization of transgenic rats resulted in production of high titer serum responses of antigen-specific heavy chain antibodies. These transgenic rats expressing heavy chain antibodies with a human VDJ region were called UniRats™.

Example 2: Immunization

Immunization with Recombinant Extracellular Domain of CD22.

Twelve UniRat animals (6 HC27, 6 HC28) were immunized with recombinant human CD22 protein. The animals were immunized according to standard protocol using a Titermax/Alhydrogel adjuvant. Recombinant extracellular domain of CD22 was purchased from R&D Systems and was diluted with sterile saline and combined with adjuvant. The immunogen was combined with Titermax and Alhydrogel adjuvants. The first immunization (priming) with immunogen in Titermax was administered in the left and right legs. Subsequent boosting immunizations were done in the presence of Alhydrogel and three days before harvest boosts were performed with immunogens in PBS. Serum was collected from rats at the final bleed to determine serum titers.

Serum Titer Results

Figure 6:
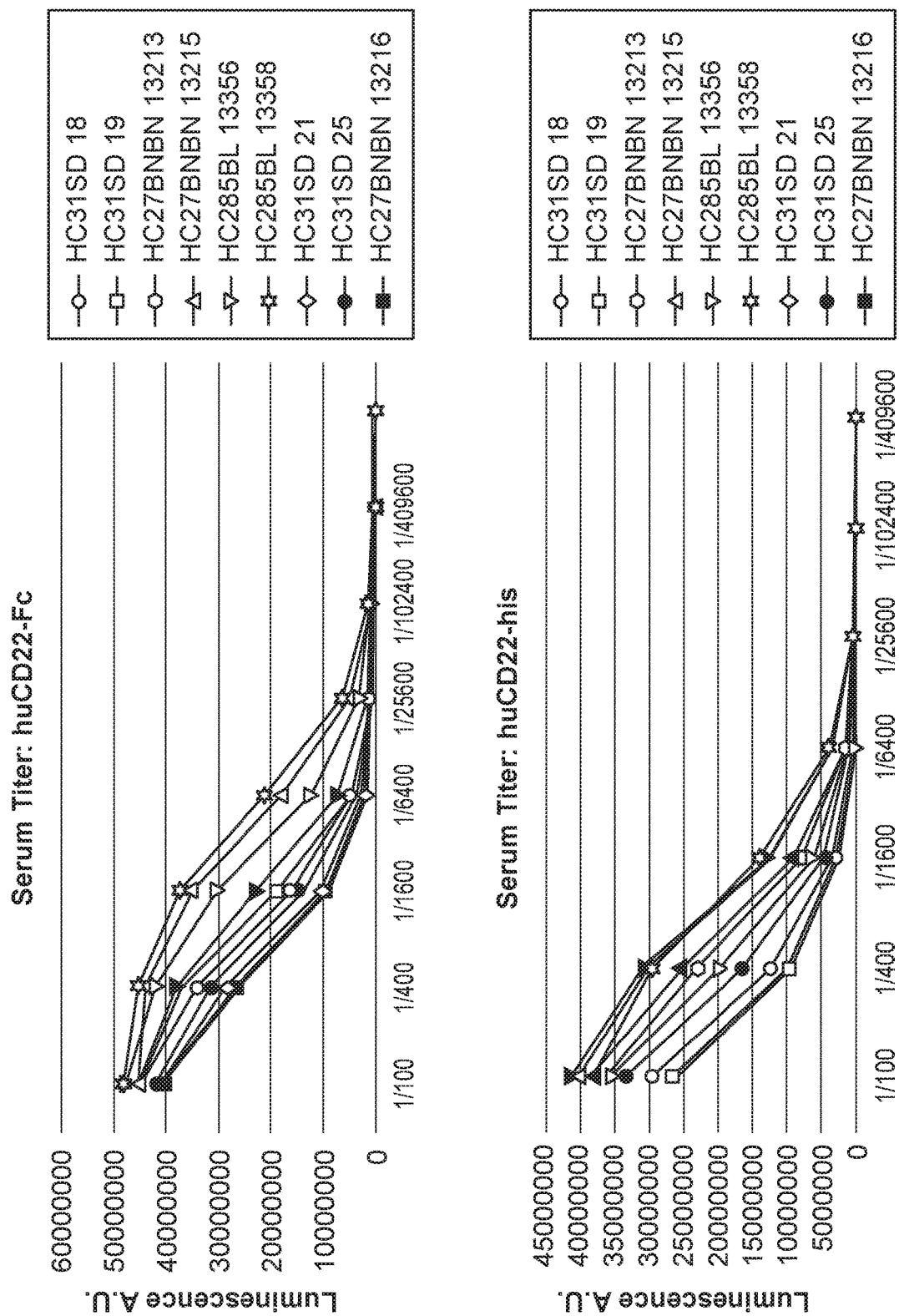
FIG. 6 is a series of graphs showing serum titer as a function of dilution.
Figure 6:
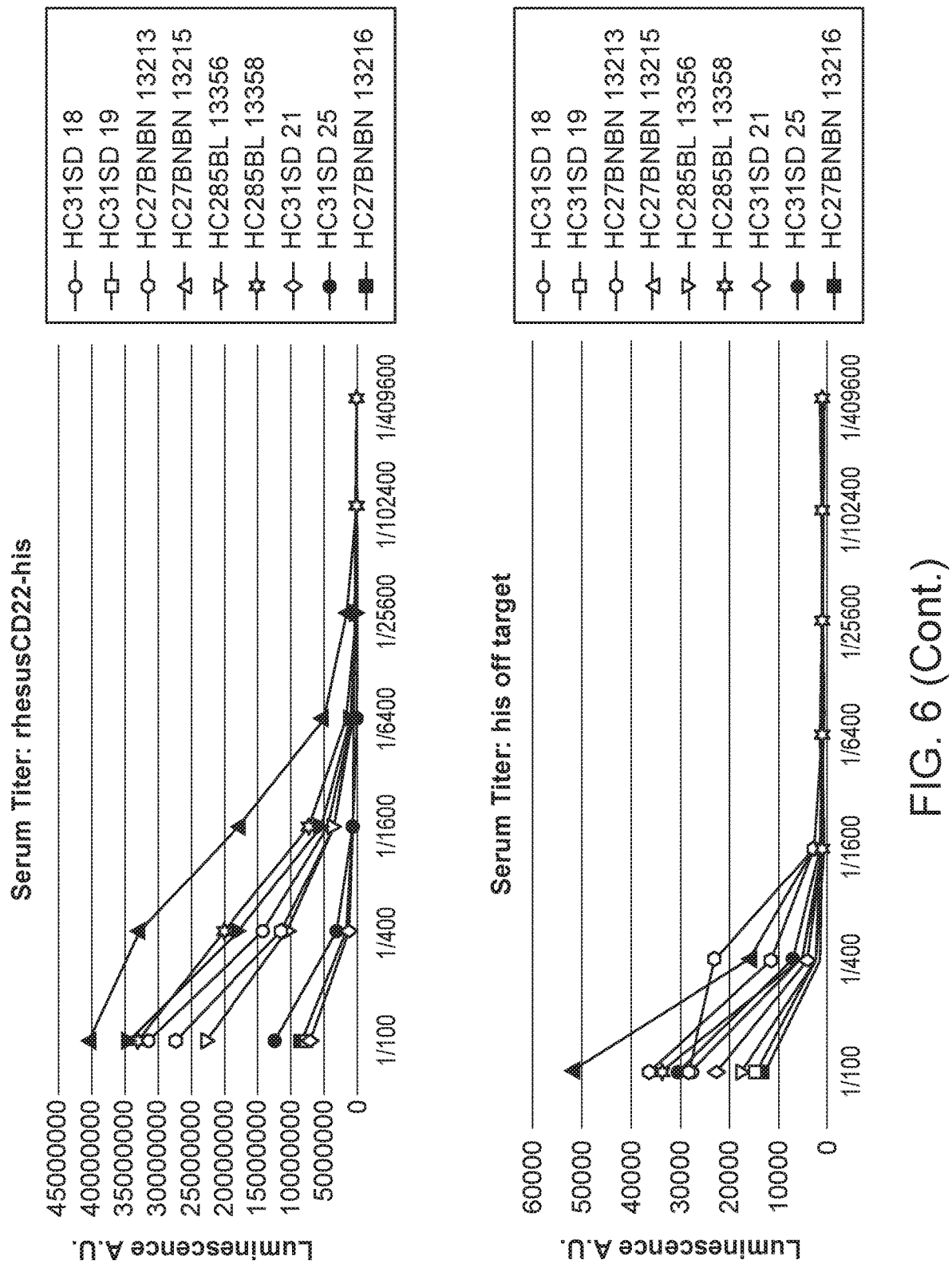

Serum titer summary information is shown in FIG. 6. In the graphs depicted in FIG. 6, each line represents an individual animal. The legends of the graphs show the ID number of each individual animal Binding activity for an 8-point dilution series of serum was tested by ELISA against a huCD22+Fc protein, huCD22+His tag, rhesus CD22+His tag protein protein, and a His tag off-target protein. Among this group of animals, a range of serum reactivity levels to both human and rhesus CD22 protein was observed. A serum response to the His protein tag was also observed.

Example 3: Binding to CD22-Expressing Cell Lines

FIG. 4 summarizes target binding activity of the anti-CD22 heavy chain-only antibodies described herein. Column 1 indicates the Clone ID number of the anti-CD22 heavy chain-only antibody. Column 2 indicates the binding affinity to protein (KD) measured in molarity. Column 3 indicates the dissociation constant of binding to protein (K-off rate) measured in seconds. Column 4 indicates binding to Daudi cells measured as fold over background MFI signal. Column 5 indicates binding to CHO cells stably expressing cyno CD22 measured as fold over background MFI signal. Column 6 indicates binding to CHO cells that do not express CD22 protein measured as fold over background MFI signal.

Figure 5C:
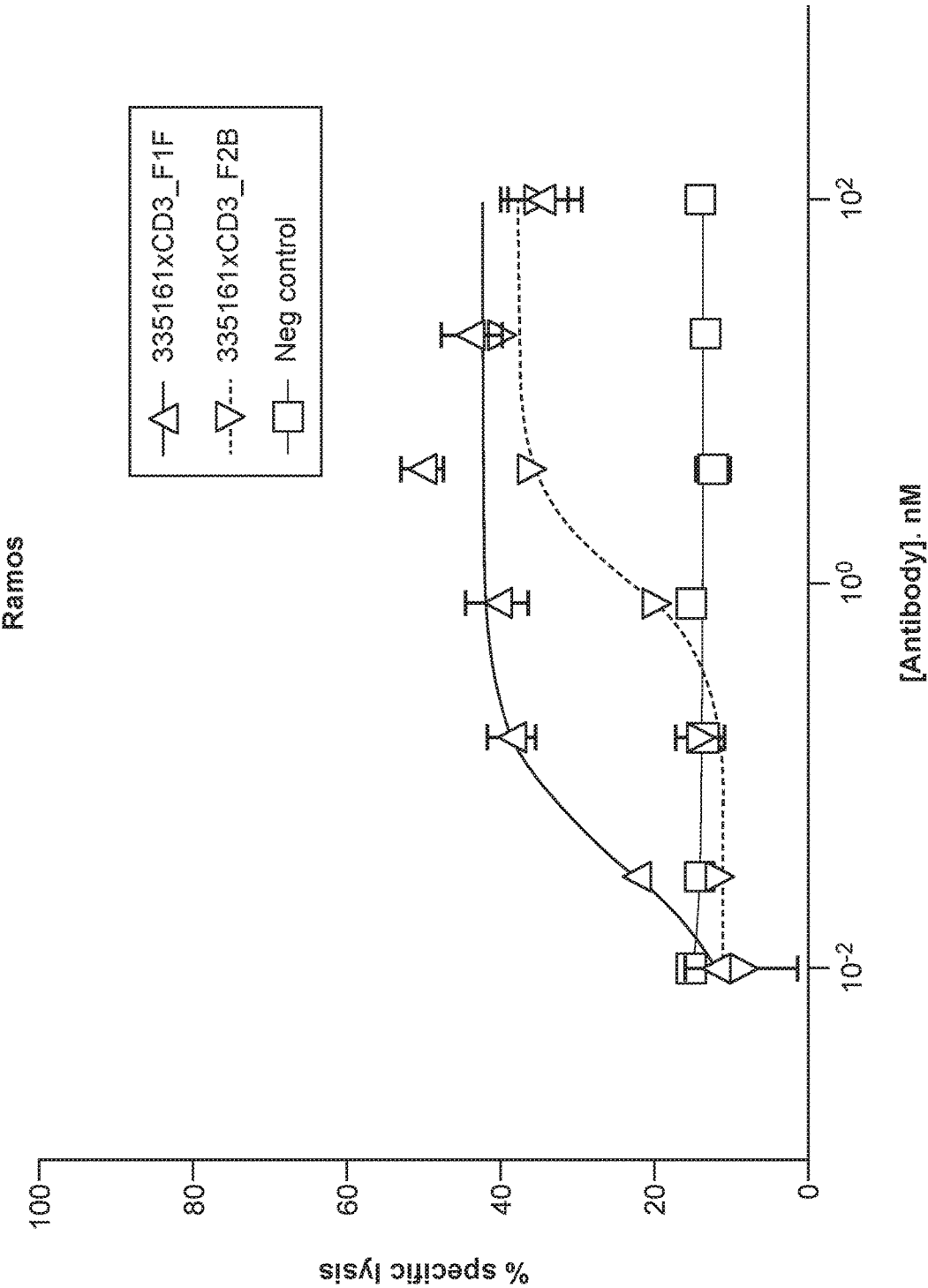
FIG. 5C is a graph depicting percent specific lysis as a function of antibody concentration for Ramos cells.
Figure 5D:
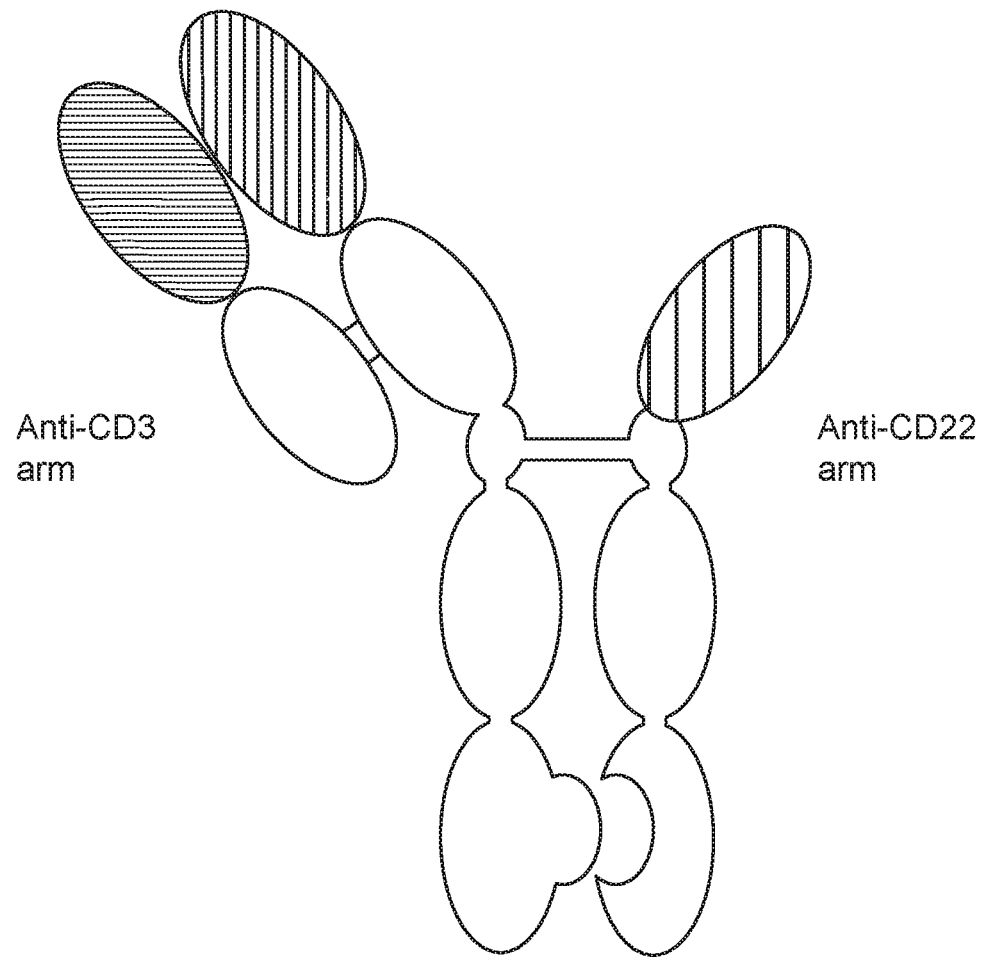
FIG. 5D is a schematic illustration of a bispecific anti-CD22×anti-CD3 in accordance with one embodiment of the invention.

Example 4: Bispecific Antibody Mediated Killing of Human Tumor Cells Through Redirection of Activated T Cells Three different CD22-positive Burkitt's lymphoma tumor cell lines (Daudi, Raj i, and Ramos) were dye-labeled and incubated with increasing amounts of bispecific antibody in the presence of pre-activated human T cells. The bispecific antibody was composed of an anti-CD3 binding arm paired with the anti-CD22 VH binding domain, as depicted schematically in FIG. 5D. The negative control antibody included a VH binding domain that did not bind to CD22. CD22-negative K562 cells exhibited no specific lysis (data not shown). The data from three bispecific antibodies incorporating three different anti-CD22 heavy chain-only binding domains paired with the same anti-CD3 binding domain are shown in FIG. 5A, compared to a negative control, and demonstrate antibody-mediated killing of CD22 positive Daudi tumor cells through redirection of activated T cells. The data from two bispecific antibodies incorporating the same anti-CD22 heavy chain-only binding domain paired with two different anti-CD3 binding domains are shown in FIG. 5B, compared to a negative control, and demonstrate antibody-mediated killing of CD22 positive Raji tumor cells through redirection of activated T cells. The data from two bispecific antibodies incorporating the same anti-CD22 heavy chain-only binding domain paired with two different anti-CD3 binding domains are shown in FIG. 5C, compared to a negative control, and demonstrate antibody-mediated killing of CD22 positive Ramos tumor cells through redirection of activated T cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A heavy chain-only antibody binding to CD22 comprising a heavy chain variable region comprising:
   (a) a CDR1 sequence of any one of SEQ ID NOs: 2-10; and
   (b) a CDR2 sequence of the formula:

X7 X8 Y X9 G X10 X11 where X7 is I or V;
   X8 is Y or H;
   X9 is S or T;
   X10 is A, V or S; and
   X11 is T or A; and (c) a CDR3 sequence of the formula:

X12 R X13 D S S X14 W R S where X12 is T, A or K;
   X13 is D or E; and
   X14 is N or S.

2. The heavy chain-only antibody of claim 1, wherein the CDR1, CDR2, and CDR3 sequences are present in a human VH framework.

3. The heavy chain-only antibody of claim 1, further comprising a heavy chain constant region sequence.

4. The heavy chain-only antibody of claim 3, wherein the heavy chain constant region sequence lacks a CH1 sequence.

5. The heavy chain-only antibody of claim 3, wherein the heavy chain constant region sequence comprises a CH2 domain and a CH3 domain.

6. The heavy chain-only antibody of claim 1, further comprising a human IgG4 Fc region.

7. The heavy chain-only antibody of claim 1, further comprising a variant human IgG4 Fc region.

8. The heavy chain-only antibody of claim 1, which is multi-specific.

9. The heavy chain-only antibody of claim 8, which is bispecific.

10. The heavy chain-only antibody of claim 8, having binding affinity to an effector cell.

11. The heavy chain-only antibody of claim 8, having binding affinity to a T-cell antigen.

12. The heavy chain-only antibody of claim 11, having binding affinity to CD3.

13. A polynucleotide encoding the heavy chain-only antibody of claim 1.

14. A method for the treatment of a B-cell disorder characterized by expression of CD22, comprising administering to a subject with said disorder the heavy chain-only antibody of claim 1.

* * * * *